(12) United States Patent
Milanovski et al.

(10) Patent No.: US 6,770,190 B1
(45) Date of Patent: Aug. 3, 2004

(54) METHOD OF ELECTROCHEMICAL ANALYSIS OF AN ANALYTE

(75) Inventors: Yevgeni Yurevich Milanovski, Moscow (RU); Dmitri Alexandrovich Farmakovski, Cambridge (GB); Vladimir Rurikovich Cherkasov, Cambridge (GB); Olga Leonardova, Cambridge (GB); Yuri Sergeyevich Biryukov, deceased, late of Moscow (RU), Nadejda Biryukov, legal representative

(73) Assignee: Sensor-Tech Limited, St. Helier (GB)

( * ) Notice: Subject to any disclaimer, the term of this patent is extended or adjusted under 35 U.S.C. 154(b) by 0 days.

(21) Appl. No.: 09/763,345

(22) PCT Filed: Aug. 24, 1999

(86) PCT No.: PCT/GB99/02785

§ 371 (c)(1),
(2), (4) Date: May 29, 2001

(87) PCT Pub. No.: WO00/11473

PCT Pub. Date: Mar. 2, 2000

(30) Foreign Application Priority Data

Aug. 24, 1998 (RU) .......................................... 98116346

(51) Int. Cl.[7] ............................................ G01N 27/327
(52) U.S. Cl. ................................................ 205/777.5
(58) Field of Search ............................ 205/775, 777.5, 205/414, 422, 424, 317; 204/403.01, 403.14, 403.03, 403.04

(56) References Cited

U.S. PATENT DOCUMENTS 4,839,017 A * 6/1989 Taniguchi et al. ...... 204/403.06
5,312,762 A    5/1994 Guiseppi-Elie

FOREIGN PATENT DOCUMENTS

| EP | 0 193 154 A | 9/1986 | |
|---|---|---|---|
| GB | 2276724 A | * 10/1994 | ......... G01N/33/543 |
| WO | WO 89 11649 A | 11/1989 | |
| WO | WO 98 35232 A | 8/1998 | |

OTHER PUBLICATIONS

Guiseppi–Elie, A. et al., "Electroconductive polymer thin films with internal bioactive moieties for biosensor applications," Polym. Mater. Sci. Eng. (1995), 72, 404–5 (XP000853822).

* cited by examiner

*Primary Examiner*—Alex Noguerola
(74) *Attorney, Agent, or Firm*—Wolf, Greenfield & Sacks, P.C.

(57) ABSTRACT

A sensing electrode for use in methods of electrochemical analysis comprising an electrically conducting electrode coated with an electroconductive polymer membrane having immobilised therein or absorbed thereto adaptor molecules avidin, streptavidin, anti-fitc antibodies through which the sensing electrode can be made specific for an analyte under test by the binding of receptors specific for the analyte.

42 Claims, 4 Drawing Sheets

A

B

A  B

A  B  C

A  B  C

A  B

METHOD OF ELECTROCHEMICAL ANALYSIS OF AN ANALYTE

RELATED APPLICATIONS

Figure 1:
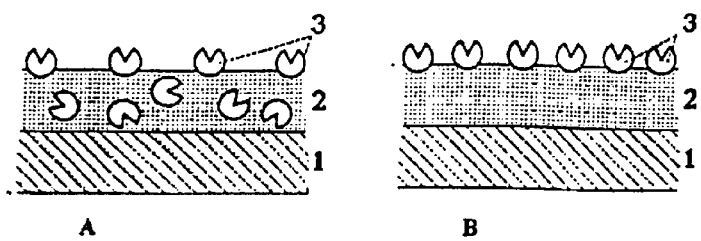

This application claims the benefit under 35 U.S.C. §120 or U.S.C. §365(c) of PCT International application PCT/GB99/02785 designating the United States of America, and filed Aug. 24, 1999, of which this application is a national stage filing under 35 U.S.C. §371, was published under PCT Article 21(2) in English.

Foreign priority benefits are claimed under 35 U.S.C. §1 19(a)–(d) or U.S.C. §365(b) of Russian application number 98116346 filed Aug. 24, 1998, which designated at least one country other than the United States.

The invention relates to methods of electrochemical detection of analytes and to sensing electrodes for use in methods of electrochemical detection.

Electrochemical analysis of analytes, such as various antigens, antibodies, DNA molecules etc, in biological fluids using biosensors is one of the most promising and attractive methods of instrument analysis. The sustained interest and large number of publications in this field are explained by a number of basic advantages of the method, namely high sensitivity, simplicity and the use of relatively simple and inexpensive equipment.

It is known in the art to construct biosensor devices based on the use of electroconductive polymer films, such as polypyrrole or polythiophene, which transduce a chemical signal associated with the presence of an analyte into a measurable electrical signal (see [1] and [2]).

EP-A-0 193 154 describes an electrode for use in electrochemical detection, the electrode being coated with a polypyrrole or polythiophene film. Bioreceptors complementary to the analyte to be tested are adsorbed onto the surface of the electroconductive polymer film after polymerisation. WO 89/11649 describes an alternative process for the production of polymeric electrodes for use in electrochemical assays. In this process bioreceptor molecules having the desired binding specificity are incorporated into a film of electroconductive polymer during polymerisation. Using the processes described in EP-A-0 193 154 and WO 89/11649 for each given assay it is necessary to synthesise a different sensing electrode having immobilized bioreceptors capable of specifically binding to the analyte for which one wants to test.

The applicants' published application PCT/GB98/00548 describes a potentiometric method of electrochemical analysis using an electrochemical sensing electrode comprising a metallic potentiometric electrode again coated with a layer of electroconductive polymer containing immobilised bioreceptor molecules which bind specifically to the analyte under test. The presence of analyte is indicated by a change in surface charge of the sensing electrode upon binding of analyte to the immobilised bioreceptors. The analyte detection procedure is carried out by first assembling an electrochemical cell comprising the sensing electrode and a reference electrode connected together by means of a measuring device immersed in a working buffer solution of fixed pH. A base value of potential difference between the sensing electrode and the reference electrode is recorded, the sensing and reference electrodes are then brought into contact with a solution of higher ionic strength suspected of containing the analyte but with pH the same as the working buffer and potential difference is again recorded. The sensing and reference electrodes are finally transferred to clean working buffer and potential is again recorded. The change in potential difference between the sensing electrode and the reference electrode resulting from a change in ionic strength of the buffer at constant pH in the presence of analyte is proportional to the concentration of analyte.

As shown in references [13, 14, 15, 16] and in [3], the response (amount and rate of potential change) of the sensing electrode with polymer film containing bioreceptors to a step-change in ionic strength of the ambient solution (so-called "ion-step" procedure) is to a large extent determined by the charge on the polymer film. Apart from the material from which it is made, the polymer film charge is determined by the charge of the receptor molecules bound in it. If the receptor charge changes as a result of an affinity reaction with a specific analyte, the response of the sensing electrode will also change as a result of the ion-step procedure carried out after contact between the sensing electrode and the test fluid. It should be noted that, because of the amphoteric nature of the majority of analytes, the receptor charge depends on the pH of the solution and it is therefore very important to maintain a constant pH of the solution during the ion-step procedure.

Thus, in the previously described methods, based on measurement of the change in response of the sensing electrode to the ion-step procedure carried out before and after contact between the sensing electrode and test fluid, it is possible to make a determination as to the presence in the test fluid of analyte specific to the receptors bound on the sensing electrode. In the ideal case, the variation in the charge of the receptors in the membrane and, hence, the change in the sensing electrode response is directly proportional to the concentration in the test fluid of analyte specific to the receptors bound on the sensing electrode. However, in real conditions, the charge of the same analyte can vary considerably, which produces inconsistent quantitative results. Moreover, the affinity reactions are not always accompanied by a change in receptor charge. This normally occurs when testing small or non-charged antigens [14].

In summary, the shortcomings of the prior art methods of electrochemical detection based on the use of electroconductive polymer electrodes include complexity and limited amenability to industrialisation of the sensing electrode manufacturing process, inconsistency of the characteristics of the sensing electrodes obtained, limited ability to store the sensing electrodes without loss of performance. In addition, the previously described protocols for electrochemical detection, particularly the method described in PCT/GB98/00548, are of limited use for the detection of small and non charged molecules or molecules whose isoelectric point is close to the isoelectric point of the receptors immobilised on the surface of the sensing electrode.

The present invention provides a method of electrochemical analysis of an analyte in a sample which is to a large extent free of the shortcomings inherent in the methods described above in that it widens the scope of application by virtue of the ability to analyse small and non-charged molecules, provides strictly quantitative results, makes the electrode manufacturing process more amenable to industrial production methods, increases the productivity of the analysis, improves reproducibility and therefore enhances reliability of the results obtained.

Thus, in a first aspect the invention provides a sensing electrode for use in methods of electrochemical detection of an analyte, the sensing electrode comprising an electrically conductive electrode coated with an electroconductive polymer with adaptor molecules selected from the group consisting of avidin, streptavidin, anti-FITC antibodies and a molecule capable of binding to at least one class of receptor molecules immobilised therein or adsorbed thereto.

One of the principal problems inherent in electrochemical analysis methods using sensing electrodes is the problem of retention over time of the native properties of the receptors fixed on the sensing electrodes. Relative progress has been achieved in this field only for a limited number of enzyme sensing electrodes [7]. For the majority of electrochemical sensing electrodes using refined receptors known in the literature [8, 9, 10], their useful storage life is simply not stated. The retention of the native properties of immobilised receptors is particularly critical where antibodies are used as the receptors, which is attributable to their inherent high degree of conformational variability.

In contrast, it is known that antibodies and other biomolecules retain their useful properties over very long periods of time when stored in the form of concentrated solutions; therefore the problem of prolonged storage of the sensing electrodes without loss of working characteristics may be overcome by rapid immobilisation of receptors before use or even during the electrochemical detection procedure.

This problem is solved in the declared invention by use of so-called adaptor molecules which are immobilized in or adsorbed to the electroconductive polymer. The purpose of the adaptor molecules is to link receptor molecules specific to the analyte under test to the surface of the sensing electrode. As will be discussed below, with the use of adaptor molecules it is possible to temporally separate steps in the production of the sensing electrodes. Thus, it is feasible to manufacture the electrodes with immobilised/adsorbed adaptor molecules, store them for an extended period of time and then fix the specific receptors onto the electrode either before or during the electrochemical analysis. With the selection of appropriate adaptor molecules it is also possible to manufacture 'universal' sensing electrodes containing adaptor molecules capable of binding to a whole range of different receptor molecules. Specificity for the analyte under test is conferred on the 'universal' sensing electrode simply by binding to the adaptor molecules receptors of the appropriate specificity. It is therefore no longer necessary to incorporate receptors of the desired specificity during the electrodeposition process.

The proteins avidin and streptavidin are preferred for use as adaptor molecules. Avidin, a protein obtained from raw eggs, consists of four identical peptide sub-units, each of which has one site capable of bonding with a molecule of the co-factor biotin. Biotin (vitamin H) is an enzyme co-factor present in very minute amounts in every living cell and is found mainly bound to proteins or polypeptides. The ability of biotin molecules to enter into a binding reaction with molecules of avidin or streptavidin (a form of avidin isolated from certain bacterial cultures, for example Streptomyces aviation) and to form virtually non-dissociating "biotin-avidin" complexes during this reaction (dissociation constant $\sim 10^{-15}$ Mol/l) is well known [11, 12].

Investigations carried out by the authors of the declared invention have shown that avidin and streptavidin immobilised in an electroconductive polymer film, retain their native properties for an extended period of time (at least one year and possibly longer) and can be used throughout this period to link with biotin conjugated receptors. Techniques which allow the conjugation of biotin to a wide range of different molecules are well known in the art. Thus sensing electrodes with immobilised avidin or streptavidin can easily made specific for a given analyte merely by binding of the appropriate biotinylated receptors.

Although avidin and streptavidin are the preferred adaptor molecules it is within the scope of the invention to use alternative adaptor molecules, in particular molecules capable of specifically binding to at least one class of receptor molecules. Included within this group of alternative adaptor molecules are protein A, protein G and lectins. These molecules all share the ability to bind to at least one class of receptor molecules, by which is meant that they are able to specifically bind to a common binding site motif which is present in each member of a group of receptor molecules, the dissociation constant for the binding interaction being less than $10^{-8}$ Mol/l. By way of example, protein A (a 42 kD polypeptide isolated from *Staphyloccus aureus* or obtained by recombinant DNA technology) binds to immunoglobulins, particularly IgG, from a wide range of mammalian species at the Fc region; and protein G (IgG Fc receptor Type III, see Bjorck, L. and Kronvall, G., J. Immunol., 133, 969 (1984)) also binds to the Fc region of IgG molecules from a wide range of mammalian species. Lectins are proteins which bind to sugar moieties which may be present on glycoproteins or carbohydrates. Each type of lectin has specificity for a given sugar moiety and thus will be able to bind a range of glycoproteins or complex carbohydrates carrying the correct sugar moiety.

In a still further embodiment anti-FITC antibodies can be used as the adaptor molecules. In this embodiment, the specificity of the sensing electrode for analyte can be conferred by binding to the anti-FITC antibodies FITC labelled receptors of the appropriate specificity.

The use of adaptor molecules in/on the electroconductive polymer film also considerably improves the reliability of the results obtained during electrochemical analysis by reducing non-specific interactions of the components of the test solution during contact with the sensing electrode, which is linked to the blocking of the free surface of the electroconductive polymer by adaptor molecules. The use of adaptor molecules also increases the technical efficiency of the sensing electrode manufacturing process, for example by eliminating the need for an additional surface blocking procedure.

The potentiometric sensing electrodes of the invention are inexpensive to manufacture and so for convenience can be produced in a disposable format, intended to be used for a single electrochemical detection experiment or a series of detection experiments and then thrown away. The invention further provides an electrode assembly including both a sensing electrode and a reference electrode required for electrochemical detection. As will be discussed below, suitable reference electrodes include silver/silver chloride and calomel electrodes. Conveniently, the electrode assembly could be provided as a disposable unit comprising a housing or holder manufactured from an inexpensive material equipped with electrical contacts for connection of the sensing electrode and reference electrode.

The sensing electrodes of the invention can be used in a wide range of electrochemical analysis procedures, including (but not limited to) double antibody sandwich assays for antigens, double antigen sandwich assays for antibodies, competitive assays for antigens, competitive assays for antibodies, serological assays for the determination of human antibodies (e.g. Rubella IgG antibodies using labelled antihuman antibodies) and IgM assays (e.g. IgM-Rubella antibodies).

In a second aspect the invention provides a method of producing a sensing electrode for use in methods of electrochemical detection of an analyte, the sensing electrode comprising an electrically conductive electrode coated with an electroconductive polymer with adaptor molecules selected from the group consisting of avidin, streptavidin and a molecule capable of binding to at least one class of receptor molecules immobilized therein, the method comprising the steps of:

(a) preparing an electrochemical polymerisation solution comprising monomeric units of the electroconductive polymer and adaptor molecules, (b) immersing the electrode to be coated in the electrochemical polymerisation solution, and (c) applying a cyclic electric potential between the electrode and the electrochemical polymerisation solution to coat the electrode by electrochemical synthesis of the polymer from the solution, said cyclic electric potential being applied for at least one full cycle.

The invention further provides a method of producing a sensing electrode for use in methods of electrochemical detection of an analyte in a sample, the electrode comprising an electrically conductive electrode coated with an electroconductive polymer with adaptor molecules selected from the group consisting of avidin, streptavidin and a molecule capable of binding to at least one class of receptor molecules adsorbed thereto, the method comprising steps of:

(a) preparing an electrochemical polymerisation solution comprising monomeric units of the electroconductive polymer, (b) immersing the electrode to be coated in the electrochemical polymerisation solution, (c) applying a cyclic electric potential between the electrode and the electrochemical polymerisation solution to coat the electrode by electrochemical synthesis of the polymer from the solution, said cyclic electric potential being applied for at least one full cycle; and (d) contacting the coated electrode with a solution comprising adaptor molecules such that the adaptor molecules are adsorbed onto the electroconductive polymer coating of the electrode.

According to the methods of the invention a film of electroconductive polymer is deposited onto the surface of an electrically conductive electrode by electrochemical synthesis from a monomer solution. The electrically conductive electrode is preferably a standard potentiometric electrode possessing metallic or quasi-metallic conductivity which is stable in aqueous media. As will be illustrated in the examples included herein, electrodeposition of the electroconductive polymer film is carried out using a solution containing monomers, a polar solvent and a background electrolyte. Pyrrole, thiophene, furan or aniline are the preferred monomers. Deionised water is preferably used as the polar solvent.

As is well krown to persons skilled in the art, electrocenductive molymers are often doped at the electrochemical synthesis stage in order to modify the structure and/or conduction Properties of the polymer. A typical dopant anion is sulphate ($SO_4^{2-}$) which is incorporated during the polymerisation process, neutralising the positive charge on the polymer backbone. Sulphate is not readily released by ion exchange and thus helps to maintain the structure of the polymer. In the present invention it is preferred to use dopant anions having maximum capability for ion exchange with the solution surrounding the polymer in order to increase the sensitivity of the electrodes. This is accomplished by using a salt whose anions have a large ionic radius as the background electrolyte when preparing the electroehemical oolymerisation solution. Suitable salts whose anions knave large ionic radius include sodium dodecyl sulphate and dextran sulphate. The concentration of these salts in the electrochemical polymerisation solution is varied according to the type of test within the range 0.005–0.05 M.

As reported in a number of papers [4, 5], the ease with which ion exchange takes place and the rapidity with which ion equilibrium is attained for electroconductive polymers immersed in a solution are essentially dependent on the size of the dopant anion introduced at the electrodeposition stage: the larger the ionic radius of the dopant anion, the more readily ion-exchange reactions take place and the more rapidly a state of equilibrium is reached. This is directly linked to the valuse and rate of change of the potential of the "metal electrode-electroconductive polymer" system in response to variation in the ion composition of the solution [6].

The electroconductive polymer membrane performs a dual function, serving both to bind the receptor to the surface of the sensing electrode, and to render the sensing electrode sensitive to variations in the composition of the buffer solution. In particular, changes in the composition of the buffer solution which affect the redox composition of the electroconductive polymer result in a corresponding change in the steady state potential of the sensing electrode.

Adaptor molecules may either be immobilized in the electroconductive polymer film at the electrochemical synthesis stage by adding adaptor molecules to the electrochemical polymerisation solution or may be adsorbed onto the surface of the electroconductive polymer film after electrochemical polymerisation. In the former case, a solution of adaptor molecules may be added to the electrodeposition solution immediately before the deposition process. The deposition process works optimally if the storage time of the finished solution does not exceed 30 minutes. Depending on the particular type of test, the concentration of adaptor molecules in the solution may be varied in the range 5.00–100.00 $\mu$/ml. Procedures for electrodeposition of the electroconductive polymer from the solution containing adaptor molecules are described in the examples included herein. On completion of electrodeposition process, the sensing electrode obtained may be rinsed successively with deionised water and 0.01 M phosphate-saline buffer solution and, depending on the type of test, may then be placed in a special storage buffer solution containing microbial growth inhibitors or bactericidal agents (e.g gentamicin), or dried in dust-free air at room temperature.

Where the adaptor molecules are to be adsorbed after completion of the electrodeposition process the following protocol may be used (although it is hereby stated that the invention is in no way limited to the use of this particular method), the sensing electrode is first rinsed with deionised water and placed in freshly prepared 0.02M carbonate buffer solution, where it is held for 15–60 minutes. The sensing electrode is then placed in contact with freshly-prepared 0.02M carbonate buffer solution containing adaptor molecules at a concentration of 1.00–50.00 $\mu$g/ml, by immersing the sensing electrode in a vessel filled with solution, or by placing a drop of the solution onto the surface of the sensing electrode. The sensing electrode is incubated with the solution of adaptor molecules, typically for 1–24 hours at +4° C. After incubation, the sensing electrode is rinsed with deionised water and placed for 1–4 hours in a 0.1M phosphate-saline buffer solution. Depending on the type of test, the sensing electrode may then be placed either in a special storage buffer solution containing microbial growth inhibitors or bactericidal agents, or dried in dust-free air at room temperature.

When the adaptor molecules are avidin or streptavidin, the above-described methods of the invention for producing a sensing electrode may optionally comprise a further step of contacting the coated electrode with a solution comprising specific receptors conjugated with biotin such that said biotinylated receptors bind to molecules of avidin or streptavidin immobilised in or adsorbed to the electroconductive polymer coating of the electrode via a biotin/avidin or biotin/streptavidin binding interaction.

Research carried out both by the authors of the declared invention, and by others [12], has shown that the biotinylation of receptors under optimal conditions does not alter their properties (affinity, storage qualities, etc.) compared with their non-biotinylated equivalents.

Conjugation of biotin with the corresponding receptors, a process known to those skilled in the w art as biotinylation, can be carried out using one of the known procedures, for example as described in [12]. In addition, a number of ready-made preparations of biotinylated antibodies of different specificity are commercially available, e.g. Anti-Human IgG or Anti-Human IgA goat biotin-labelled antibodies made by Calbiochem-Novabiochem, USA.

One of the significant advantages of using biotinylated receptors is the ability to vary the specificity of the sensing electrode, by producing a reaction between the avidin or streptavidin bound on the sensing electrode and the corresponding biotinylated receptors. As discussed previously, the sensing electrode with bound avidin/streptavidin is in effect a 'universal sensing electrode' and specificity to the desired molecules under test is conferred by the binding of the appropriate biotinylated receptors. To make the sensing electrode with bound avidin or streptavidin specific to the analyte under test, a reaction is carried out between the avidin or streptavidin bound on the sensing electrode with biotinylated receptors, for which purpose the sensing electrode is brought into contact with a solution of the latter at room temperature, either by immersing the sensing electrode in a vessel filled with solution, or by placing drop of solution on the sensing electrode surface (concentration of biotinylated receptors in the solution is generally 0.1–100 $\mu$g/ml; contact time 3–15 minutes).

The receptor molecules can be any molecule capable of specifically binding to another molecule (an analyte). Suitable types of receptors include monoclonal and polyclonal antibodies, chimaeric antibodies, fragments of antibodies which retain the ability to recognise antigen (e.g. Fab and Fab2 fragments), recombinant proteins and fragments thereof, synthetic peptides, antigens, single-strand DNA, RNA or PNA molecules, hormones, hormone receptors, enzymes, chemical compounds etc.

As discussed above, the electrochemical detection methods known in the art using potentiometric sensing electrodes are of limited use in the detection of small and non-charged antigens. In order to overcome this problem, and to obtain strictly quantitative results, use may be made of secondary receptors or competing molecules conjugated with a charge label.

Accordingly, in a further aspect the invention provides a method of electrochemical detection of an analyte in a sample, which method comprises the steps of:

(a) providing a sensing electrode having an electroconductive polymer coating, the coating having immobilised therein or adsorbed thereto receptors which specifically bind to the desired analyte to be detected in the sample;

(b) treating the sensing electrode by immersion in a test solution comprising the sample so that said desired analyte binds to said immobilised or adsorbed receptors;

(c) contacting the sensing electrode with a solution comprising secondary receptors capable of binding to said analyte at a site spatially distinct from the site of binding to the immobilised or adsorbed receptors, said secondary receptors being conjugated with a charge label;

(d) monitoring the electric potential difference between the treated sensing electrode and a reference electrode when both are immersed in an electrolyte; and (e) monitoring the electric potential difference between the sensing electrode and a reference electrode following a change in the ionic strength of the electrolyte at constant pH.

The affinity reaction steps of the above-described method are equivalent to a standard sandwich assay well known to those skilled in the art. The sandwich format of analysis is particularly useful for the detection of polyvalent antigens in which case the receptors and labelled secondary receptors used in the test are antibodies which bind to different, spatially distinct epitopes on the antigen. The sandwich format can also be used where the antigen carries two or more identical epitopes which are spatially separated. In this latter case, the receptors and labelled secondary receptors used in the test may be antibodies of identical specificity.

It is also within the scope of the invention to perform the electrochemical analysis in a competitive assay format. Therefore, the invention also provides a method of electrochemical detection of an analyte in a sample comprising the steps of:

(a) providing a sensing electrode having an electroconductive polymer coating, the coating having immobilised therein or adsorbed thereto receptors which are capable of binding to the desired analyte to be detected in the sample;

(b) treating the sensing electrode by immersion in a test solution comprising the sample so that said desired analyte binds to said immobilised or adsorbed receptors;

(c) contacting the sensing electrode with a solution comprising competing molecules capable of binding to said immobilised or adsorbed receptors, said competing molecules being conjugated with a charge label;

(d) monitoring the electric potential difference between the treated sensing electrode and a reference electrode when immersed in an electrolyte; and (e) monitoring the electric potential difference between the sensing electrode and a reference electrode following a change in the ionic strength of the electrolyte at constant pH.

Figure 5:
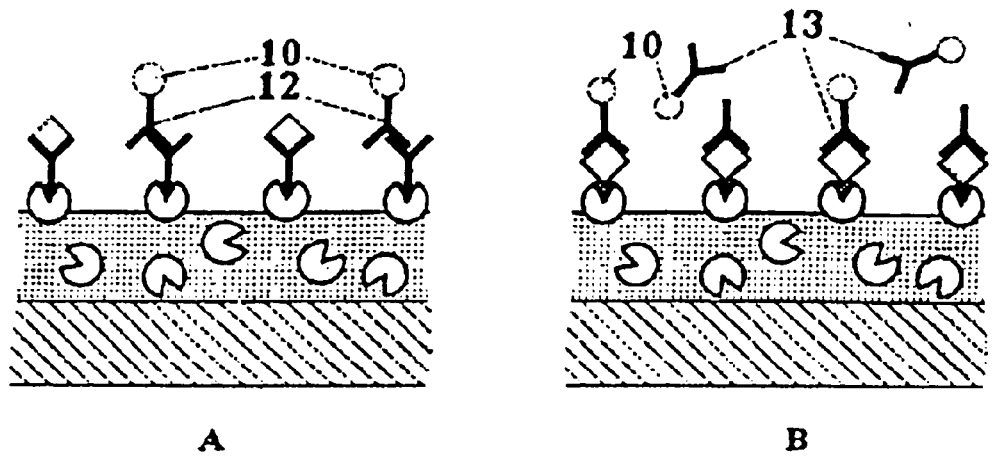
Figure 7:
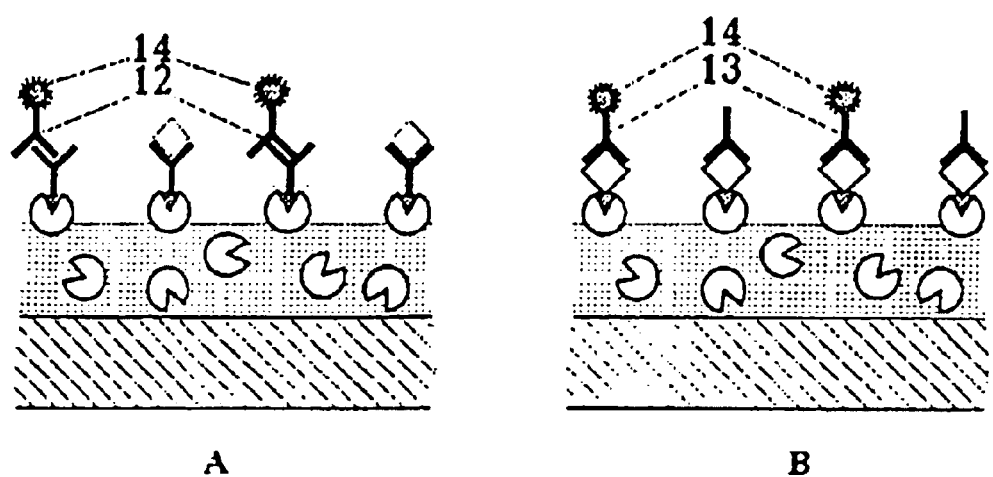

In this competitive electrochemical assay the competing molecules could be labelled analyte or labelled structural analogs of the analyte which are capable of binding to the same analyte binding site on the immcbilized/adsorbed receptors (see FIG. 5B and FIG. 7B). The use of labelled analyte as the competing molecule is particularly preferred for the detection of small analyte molecules (e.g. digoxin, as described in the examples included herein). Alternatively, the competing molecule may bind to a different site on the immobilized/adsorbed receptor. For example, if the immobilized receptor is an antibody, the competing molecule could be an anti-immunoglobulin antibody (preferably Fab-specific) or even an anti-idiotype antibody of the appropriate specificity (see FIG. 5A and FIG. 7A).

As would be readily understood by persons skilled in the art, with reference to FIGS. 5A, 5B, 7A and 7B of the present application, the competitive detection methods are usually dependent on their being an excess of receptor sites on the surface of the sensing electrode. Those receptors which do not bind analyte will be available for binding to the competing molecule. Assuming that the total number of receptor sites remains constant, the amount of bound competing molecule will be inversely proportional to the amount of analyte present.

In order to transduce the chemical signal associated with the concentration of,the analyte into a measurable electrical signal the charge label which is conjugated to the secondary receptors or competing molecules can be any charge label having the following properties:

(i) carries a net charge (positive or negative) at the pH of the electrolyte of part (d); and (ii) the magnitude of this charge changes in response to a change in the ionic strength of the electrolyte at constant pH.

Preferably the charge label is highly charged, i.e. has a net charge at the pH of the electrolyte of part (d) of greater than one electrostatic unit (e). Suitable charge labels include gold, ferrocene and latex microspheres. The magnitude of the charge on the charge label affects the redox composition of the electroconductive polymer coating on the sensing electrode such that the step change in ionic strength between steps (d) and (e) results in a detectable change in potential difference between the sensing electrode and the reference electrode. The charge label is only brought into close proximity of the electroconductive polymer on formation of receptor/analyte/secondary receptor complexes (sandwich assay) or receptor/competing molecule complexes (competitive assay). The use of a charge label thus makes it possible to obtain correct qualitative results and considerably extends the spectrum of testable analytes by virtue of the ability to test small and non-charged analytes.

Latex microspheres are the preferred type of charge label conjugated with the secondary receptors or competing molecules. Conjugation with latex microspheres may be carried out using one of the known techniques, for example as described in [17] or [18], or using special commercially available kits for the conjugation of antibodies with latex imicrospheres, for example "Carbodiimide Kit for Carboxylated Beads" made by Polysciences Inc., USA, following the protocol supplied by the manufacturer. Certain ready-made latex conjugates are commercially available from specialist manufacturers, e.g. Polysciences Inc., USA.

As an alternative to the use of a charge label, it is also possible to perform electrochemical detection procedures equivalent to those described above using secondary receptors or competing molecules conjugated with an enzyme labels in order to transduce the chemical signal associated with the concentration of the analyte into a measurable electrical signal.

Accordingly, the invention further provides a method of electrochemical detection of an analyte in a sample, which method comprises the steps of:

(a) providing a sensing electrode having an electroconductive polymer coating, the coating having immobilized therein or adsorbed thereto receptors which are capable of binding to the desired analyte to be detected in the sample;

(b) treating the sensing electrode by immersion in a test solution comprising the sample so that the said analyte binds to said immobilized or adsorbed receptors;

(c) contacting the sensing electrode with a solution comprising secondary receptors capable of binding to said analyte at a site spatially distinct from the site of binding to immobilized or adsorbed receptors, said secondary receptors being conjugated with an enzyme;

(d) monitoring the electric potential difference between the treated sensing electrode and a reference electrode when both are immersed in an electrolyte; and (e) monitoring the electric potential difference between the sensing electrode and a reference electrode following exposure to an electrolyte comprising the substrate for said enzyme.

Also within the scope of the invention is the corresponding competitive method of electrochemical detection comprising the steps of:

(a) providing a sensing electrode having an electroconductive polymer coating, the coating having immobilized therein or adsorbed thereto receptors which are capable of binding to the desired analyte to be detected in the sample;

(b) treating the sensing electrode by immersion in a test solution comprising the sample so that the said desired analyte binds to said immobilized or adsorbed receptors;

(c) contacting the sensing electrode with a solution comprising competing molecules capable of binding to said irmobilized or adsorbed receptors, said competing molecules being conjugated with an enzyme;

d) monitoring the electric potential difference between the treated sensing electrode and a reference electrode when both are immersed in an electrolyte; and e) monitoring the electric potential difference between the sensing electrode and a reference electrode following exposure to an electrolyte comprising the substrate for said enzyme.

In one embodiment of the above-described methods the enzyme conjugated to the secondary receptors or competing molecules is capable of converting a substrate which directly affects the redox composition of the electroconductive polymer coating of the sensing electrode into a product which has no detectable effect on the redox composition of the electroconductive polymer.

In an alternative embodiment, the enzyme conjugated to the secondary receptors or competing molecules is capable of converting a substrate which has no detectable effect on the redox composition of the electrochemical polymer coating of the sensing electrode to a product capable of directly or indirectly affecting the redox composition of the electroconductive polymer. An example of such an enzyme is horseradish peroxidase. One way in which the product of the enzymic reaction may indirectly affect the redox composition of the electroconductive polymer is by causing a change in the pH of the electrolyte (for this embodiment the pH of the electrolyte is not buffered). An example of an, enzyme which generates such a product is urease.

In a still further embodiment, the enzyme conjugated to the secondary receptors or the competing molecules is capable of converting a product which has no detectable effect on the redox composition of the electroconductive polymer coating of the sensing electrode into a product which is a substrate for a second enzyme, the action of the second enzyme generating a second product which directly or indirectly affects the redox composition of the electroconductive polymer.

In all embodiments the conjugated enzyme is brought into close proximity of the electroconductive polymer by formation of receptor/analyte/secondary receptor complexes (sandwich format) or by formation of receptor/competing molecule complexes (competitive format).

The conjugation of secondary receptors or competing molecules with enzyme labels may be performed by any of the techniques known in the art (see, for example [19]). Use can also be made of widely available commercial preparations of conjugates of receptors of different specificity with different enzyme labels.

All of the above methods of electrochemical detection can be performed using any type of receptor capable of specifically binding to another molecule (an analyte). Suitable types of receptors include monoclonal and polyclonal antibodies, chimaeric antibodies, fragments of antibodies which retain the ability to recognise antigen (e.g. Fab and Fab2 fragments), recombinant proteins and fragments thereof, synthetic peptides, antigens, single-strand DNA, RNA or PNA molecules, hormones, hormone receptors, enzymes, chemical compounds etc.

Regardless of whether the secondary receptors or competing molecules are conjugated with a charge or enzyme label, the maximum degree of specificity and sensitivity for all of the detection methods of the invention is achieved by performing the affinity reactions (i.e. steps (a) to (c)) in a 'sequential' format. This is particularly so when the analyte under test is a polyvalent antigen (i.e. the sandwich assay). In the sequential format the sensing electrode with bound receptors is first brought into contact with a test solution comprising the sample to be tested for the presence of the analyte. As used herein the term 'sample' includes within its scope any material which it is desired to test for the presence of analyte, including biological fluids such as whole blood, serum, plasma, urine, lymph, cerebrospinal fluid or semen, environmental fluids, materials used or produced in the food and drink industry or a dilution or extract of any of the above. The sample may also comprise a solution or extract of a solid material. The container used for the test solution may be the well of a microtiter plate, a micro-centrifuge tube or any other vessel of suitable size. The volume of test solution will generally be 5–200 $\mu$l depending on the geometrical dimensions of the sensing electrode. The contact time between the sensing electrode and test solution is typically 3–30 minutes at 15–40° C. with or without continuous mixing.

Following contact with the test solution the sensing electrode is transferred to a vessel containing solution of labelled secondary receptors. The vessel and volume of solution used are similar to those used for contact between the sensing electrode and test solution. The concentration of labelled secondary receptors or labelled competing molecules in the solution is typically 1–100 $\mu$g/ml depending on the required sensitivity of the test. Contact is made for 3–30 minutes at 15–40° C. with or without continuous mixing.

As an alternative to the 'sequential' format it is possible to substantially reduce the total test time and simplify the test procedure by performing steps (b) and (c) simultaneously by contacting the sensing electrode with test solution to which has been added the appropriate labelled secondary receptors or labelled competing molecules for a contact time of about 5–60 minutes. The concentration of labelled secondary receptors or is labelled competing molecules added to the test solution is typically 1–100 $\mu$g/ml depending on their type, specific features and required sensitivity of the test.

To eliminate possible non-specific interactions between the components of biological fluids under test and the surface of the sensing electrode, and also non-specific adsorption of labelled secondary receptors or labelled competing molecules onto the surface of the sensing electrode, which will distort the results obtained, various blocking agents may be added to the solution of labelled secondary receptors or labelled competing molecules. Suitable blocking agents include bovine serum albumin (0.5%–5%), human serum albumin (0.5–5 wt. %), dilute normal human or animal serum (5–10 vol. %), gelatin (10–50 vol. %), etc. In so doing, interaction of the labelled secondary receptors or labelled competing molecules with the sensing electrode is accompanied by simultaneous blocking of any free surface of the sensing electrode.

In all of the detection methods of the invention use can be made of sensing electrodes containing immobilized/adsorbed adaptor molecules. In particular, the receptor molecules may be attached to the surface of the sensing electrode via biotin/avidin, biotin/streptavidin, protein A/antibody, protein G/antibody, FITC/anti-FITC or lectin/sugar binding interactions.

The use of 'universal' sensing electrodes containing adaptor molecules allows the detection methods to be performed in a 'one-pot' format. In this embodiment, the affinity reactions are performed in a homogeneous solution, providing maximum contact between the interacting molecules and ensuring maximum sensitivity and minimum duration of the test. In this case, the solution of receptors and the solution of labelled secondary receptors or labelled competing molecules are added simultaneously or sequentially to the test solution comprising the sample suspected of containing the analyte in a single reaction vessel. The concentrations of receptors and labelled secondary receptors or labelled competing molecules in the test solution are typically 0.1–100 $\mu$g/ml and 1–100 $\mu$g/ml respectively. The test solution is then incubated at 15–40° C. for 5–60 minutes with or without continuous mixing to allow the binding reactions to take place. The sensing electrode containing the appropriate adaptor molecules is then brought into contact with the test solution, either by immersion into the vessel containing the test solution, or by placing a drop of test solution on the surface of the sensing electrode. The contact time between the sensing electrode and test solution is typically 3–30 minutes at 15–40° C. Measurement of the amount of analyte bound on the sensing electrode is then performed using the "ion-step" procedure or by adding the appropriate enzyme substrate depending on whether the secondary receptors or competing molecules are labelled with a charge or enzyme label.

Once all the affinity reaction steps are completed, an electrochemical measuring cell is assembled by bringing the sensing electrode and a reference electrode, connected by a measuring instrument, into contact with an electrolyte solution (also referred to herein as a working solution) and the measuring device is used to record the sensing electrode potential relative to the reference electrode over a fixed time period. Commercially available reference electrodes of suitable size, or electrodes purpose-designed for implementation of the declared invention, may be used as the reference. The measuring instrument is a standard potentiometric measuring instrument or potentiostat. PC-compatible electronic measuring instruments purpose designed for implementation of the declared invention and controlled by custom software can also be used For convenience the sensing electrode and reference electrode can be linked to the measuring instrument by means of a special holder equipped with electrical contacts for connection of the sensing electrode and reference electrode and connected to the measuring instrument by a cable or other means. A holder integral with the measuring instrument could also be used, making it possible to miniaturise the measuring system in terms of its overall dimensions.

Aqueous buffer solutions are used as the working solution: phosphate-saline, Tris-HCl, carbonate bicarbonate, acetate, borate, etc. The volume of working solution in the electrochemical cell is typically between 50 and 5000 $\mu l$ depending on the geometrical dimensions of the sensing electrode. The container for the buffer solution may be any suitably sized vessel in a material with minimal adsorption properties, e.g. the well of a standard microtiter plate. Another embodiment of the declared invention is a variant in which a low-volume (<1 cm$^3$) flow-through cell is used in conjunction with an integral holder for the sensing electrode and reference electrode, through which buffer solution can be pumped by means of a peristaltic pump or other means.

The potential of the sensing electrode relative to the reference electrode potential is recorded for a fixed time period using a chart recorder connected to a potentiometric measuring device or potentiostat, or by means of a special program where PC-compatible electronic instrumentation is used. In the latter case, the program measures the sensing electrode potential relative to the reference electrode potential at pre-determined time intervals (typically every 3–5 seconds for a total of 10–100 seconds) and displays the results in the form of points on the coordinates "sensing electrode signal-time". Recording of sensing electrode potential relative to the reference electrode potential is carried out to determine the background potential value $V_1$ of the sensing electrode, and also to evaluate the background potential drift ($\gamma$) of the sensing electrode, which is calculated by linearisation of the curve "sensing electrode signal-time" obtained using the least squares method.

If the secondary receptors or competing molecules are conjugated with a charge label, the amount of analyte bound to the sensing electrode is evaluated by changing the ionic strength of the electrolyte solution at constant pH, the so-called "ion-step" procedure.

In the ion-step procedure the ionic strength of the electrolyte solution may be modified (upwards or downwards) either by transferring the holder complete with sensing electrode and reference electrode from the initial working solution into a second working solution of the same composition but with a different ionic strength, or by adding a buffer solution of different (higher or lower) ionic strength directly to the working solution in which the sensing electrode and reference electrode are immersed. If a flow through cell is used, the ionic strength of the electrolyte solution can be modified by expelling the initial working solution from the cell using a buffer solution of different ionic strength.

Working solutions having different ionic strengths may be achieved by having different concentrations of salts, e.g. KCl, Na$_2$SO$_4$, etc., the use of which is based on the fact that they dissociate completely when added to the solution and do not bias the pH of the solution. The concentration of salts in the working solution ranges from 0.01 to 0.1 M.

If the secondary receptors or competing molecules are conjugated with an enzyme it is not necessary to perform the "ion-step" procedure. Instead, the composition of the working solution is modified by adding a suitable substrate for the enzyme. To this end, either the holder complete with sensing electrode and reference electrode can be transferred from the vessel containing the initial working solution to a vessel containing working solution plus substrate, or the substrate solution can be added directly to the original working solution in which the sensing electrode and reference electrode are immersed. If a flow-through cell is used, the composition of the working solution can be modified by expelling the initial working solution from the cell using a working solution containing substrate.

Substrates which may be used include ABTS ({2,2'-Azino-bis-[3-ethylbenzthiazoline-6-sulfonic acid]}), TMB (3,3,5,5'-Tetraethylbenzidine), DAB (3,3' Diaminobenzidine) (where the enzyme label is peroxidase), urea (where the enzyme label is urease), p-NPP (p-Nitrophenyl Phosphate), BCIP (5-bromo-4-chloro-3-indolylphosphate) (where the enzyme label is alkaline phosphatase).

The variation in sensing electrode potential relative to the reference electrode potential in response to a step change in ionic strength of the working solution or addition of an enzyme substrate is recorded for a fixed time period using a measuring instrument. Again, the recording is made either using a chart recorder connected to a potentiometric measuring device or potentiostat, or by means of a special program where PC-compatible electronic instrumentation is used. In the latter case, the program measures the sensing electrode potential relative to the reference electrode potential at pre-determined time intervals (typically every 3–5 seconds) and displays the results in the form of points on the coordinates "sensing electrode signal—time". Depending on the particular type of test, the time taken to record the variation in sensing electrode potential relative to reference electrode potential varies between 30 and 600 seconds.

In the case where the ionic strength of the buffer solution is changed, the curve obtained for the variation in sensing electrode potential relative to the reference electrode potential usually takes the form of a parabola, and represents the response of the sensing electrode to the change in ionic strength of the buffer solution, which is modulated by the total charge (isoelectric point) of the electroconductive polymer film.

If the analysis is performed as a sandwich assay, the variation in total charge of the polymer film is directly proportional to the quantity of the analyte under test. However, if the analysis is performed as a competitive assay, the variation in total charge of the polymer film is generally inversely proportional to the quantity of analyte under test.

On completion of this stage in the procedure, the final value $V_2$ of sensing electrode potential relative to reference electrode potential is determined. The following quantitative characteristics of the change in sensing electrode potential relative to the reference electrode potential can then be calculated:

1. the area (integral) described by the curve obtained for the change in sensing electrode potential relative to reference electrode potential, $S_2$:

$$S_2 = \int_{T1}^{T2} f_2(t)\,dt$$

where: T2−T1=total time period for recording of background potential drift or potential relative to the reference electrode; $f_2$—curve of "sensing electrode potential in millivolts versus time"; t—current recording time; and 2. difference in millivolts between the background and final potential of the sensing electrode:

$$\delta = V_2 - V_1$$

Based on the quantitative characteristics of the variation in sensing electrode potential in response to a change in ionic strength or composition of the working solution, a determination is made as to the quantitative content of target analyte in the test solution.

Using the values for $\gamma$, $S_2$ and/or $\delta$ obtained as described above it is possible to re-calculate the values to allow for the zero line drift γ, yielding the values $S_2^\gamma$ and/or $\delta^\gamma$, on the basis of which a determination is made of the quantity of target analyte in test solution. The corrected values $S_2^\gamma$ and $\delta^\gamma$ may be compared with a calibration curve of "analytical result versus amount of target analyte". As would be readily apparent to persons skilled in the art, data for construction of a calibration curve can be obtained in a manner similar to the procedure described above using a range of test solutions containing known amounts of the target analyte.

In a still further aspect the invention provides a method of electrochemical detection of an analyte in a sample, which method comprises the steps of:

(a) providing a sensing electrode comprising an electrically conductive electrode coated with a layer of electroconductive polymer with avidin or streptavidin immobilized therein or adsorbed thereto, said avidin or streptavidin molecules being attached to receptor molecules capable of binding the analyte to be detected attached via a biotin/avidin or biotin/streptavidin binding interaction;

(b) contacting the sensing electrode with a test solution comprising the sample so that said desired analyte binds to said immobilized or adsorbed receptor molecules;

(c) monitoring the potential of the sensing electrode relative to a reference electrode when both are immersed in an electrolyte; and (d) monitoring the potential difference of the sensing electrode relative to the reference electrode following a change in the ionic strength or composition of the electrolyte at constant pH.

No This method of electrochemical detection is of use where the binding of the target analyte to the receptor is causes a change in charge on the surface of the sensing electrode which is sufficiently large to be measurable without the need for a separate charge or enzyme label. In particular, this method is useful in the electrochemical detection of nucleic acids. Hybridisation of target nucleic acids to nucleic acid probes (e.g. oligonucleotides) attached to the surface of the sensing electrode is accompanied by a change in charge sufficient large to be detectable by the "ion-step" procedure. There is thus no need to use secondary receptors or competing molecules conjugated with charge label. Materials suspected of containing specific nucleic acids (e.g. biological fluids) may commonly be subjected to an amplification step (e.g. PCR) before being subjected to the detection procedure. It is therefore within the scope of the invention to perform the electrochemical detection of specific nucleic acids on samples which have been subjected to an amplification procedure.

The present invention will be further understood with reference to the following non-limiting Examples together with the accompanying Figures in which the principal stages of its implementation are depicted.

FIG. 1A: schematically illustrates a sensing electrode consisting of a potentiometric electrode (1) coated with a layer of electroconductive polymer (2) with avidin or streptavidin molecules (3) immobilized in the polymer layer.

FIG. 1B: schematically illustrates a sensing electrode consisting of a potentiometric electrode (1) coated with a layer of electroconductive polymer (2) with avidin or streptavidin molecules (3) adsorbed onto the layer of polymer.

FIG. 2A: illustrates the process of rendering the sensing electrode specific to an analyte (in this case antigens, medium or high molecular weight substances) through a binding reaction between the avidin or streptavidin immobilized in the polymer layer and antibodies (4) conjugated with biotin (5).

FIG. 2B: illustrates the process of rendering the sensing electrode specific to the analyte under test (in this case antibodies) through a binding reaction between avidin or streptavidin immobilized in the polymer layer and antigen (6) conjugated with biotin (5).

FIG. 2C: illustrates the process of rendering the sensing electrode specific to the analyte under test (in this case DNA molecules) through a binding reaction between avidin or streptavidin immobilized in the polymer layer and a DNA probe (7) conjugated with biotin (5).

FIG. 3A: shows the placement of the sensing electrode in contact with a test solution containing antigens (6) specific to biotinylated antibodies immobilized on the sensing electrode.

FIG. 3B; shows placement of the sensing electrode in contact with a test solution containing antibodies (4) specific to the biotinylated antigens immobilized on the sensing electrode.

FIG. 3C: shows placement of the sensing electrode in contact with a test solution containing DNA molecules (8) specific to the biotinylated DNA probes immobilized on the sensing electrode.

FIG. 4A: shows placement of the sensing electrode in contact with a solution of secondary receptors (9) conjugated with a charge label (10) and specific to the antigen under test (serological assay format, in which e.g. autoantibodies are determined by the use of anti-isotype antibodies conjugated with a charge label).

FIG. 4B: shows placement of the sensing electrode in contact with a solution of secondary receptors (11) conjugated with a charge label (10) and specific to the antibodies under test (sandwich assay format, in this case the secondary receptors are anti-isotype antibodies).

FIG. 5A: shows placement of the sensing electrode in contact with a solution of competing molecules (12) conjugated with a charge label (10) and specific to the biotinylated antibodies (competitive assay format).

FIG. 5B: shows placement of the sensing electrode in contact with a solution of competing molecules (13) conjugated with a charge label (10) and specific to w the biotinylated antigens (competitive assay format).

Figure 6:
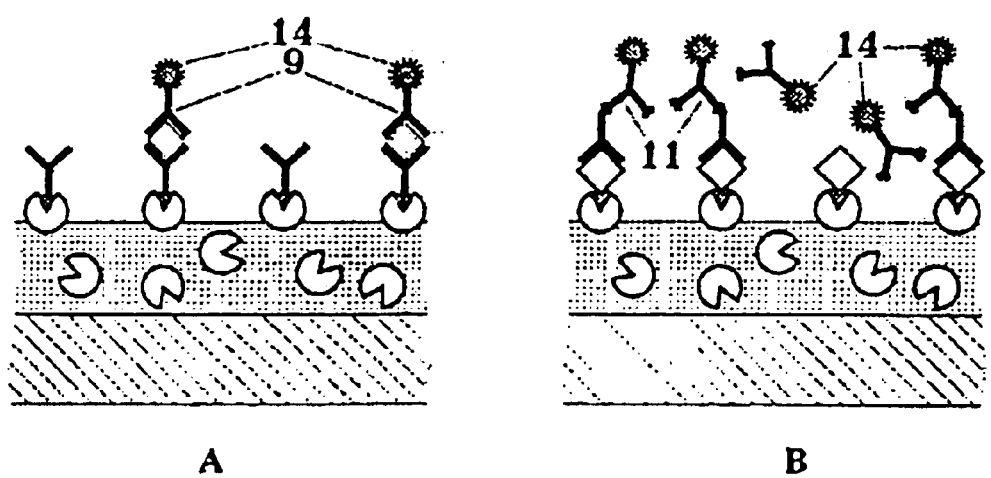

FIG. 6A: shows placement of the sensing electrode in contact with a solution of secondary receptors (9) conjugated with an enzyme (14) and specific to the antigen under test (sandwich assay format).

FIG. 6B: shows placement of the sensing electrode in contact with a solution of secondary receptors (11) conjugated with an enzyme (14) and specific to the antibodies under test (serological assay format, in which e.g. autoantibodies are determined by the use of anti-isotype antibodies conjugated with an enzyme).

FIG. 7A: shows placement of the sensing electrode in contact with a solution of competing molecules (12) conjugated with an enzyme (14) and specific to the biotinylated antibodies (competitive assay format).

FIG. 7B: shows placement of the sensing electrode in contact with a solution of competing molecules (13) conjugated with an enzyme (14) and specific to the biotinylated antigens (competitive assay format).

Figure 2:
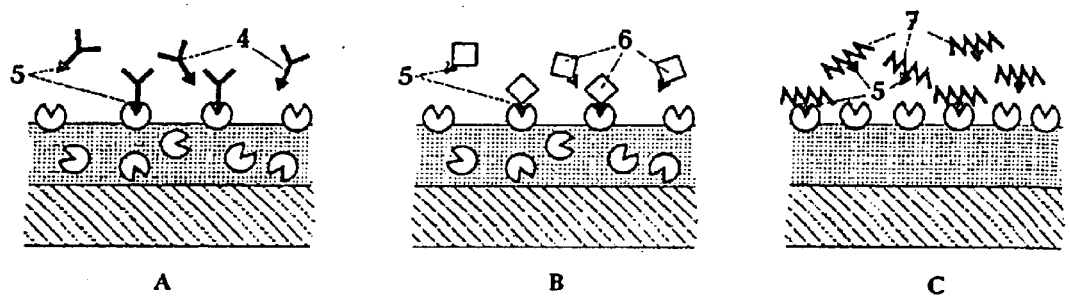
Figure 3:
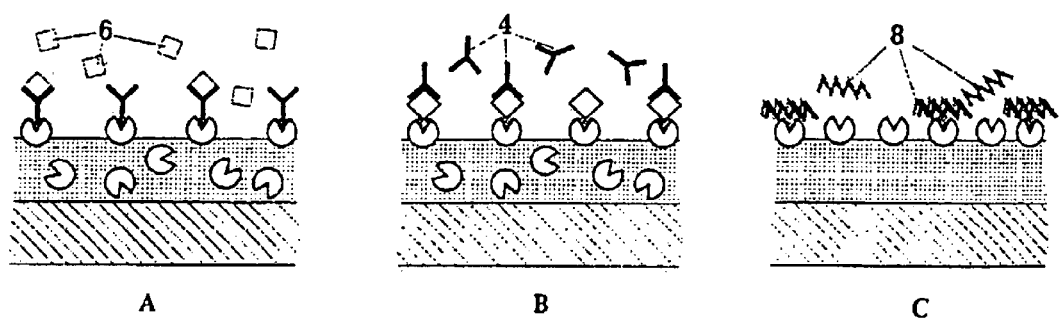
Figure 4:
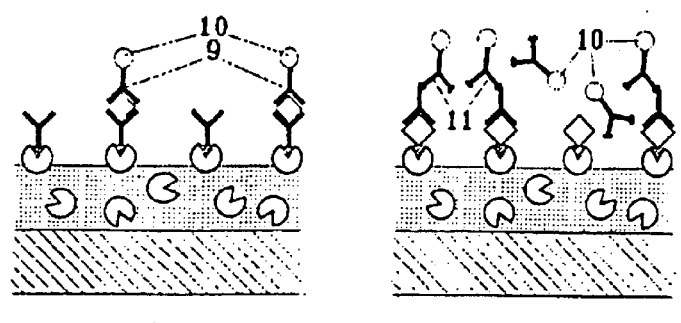
Figure 8:
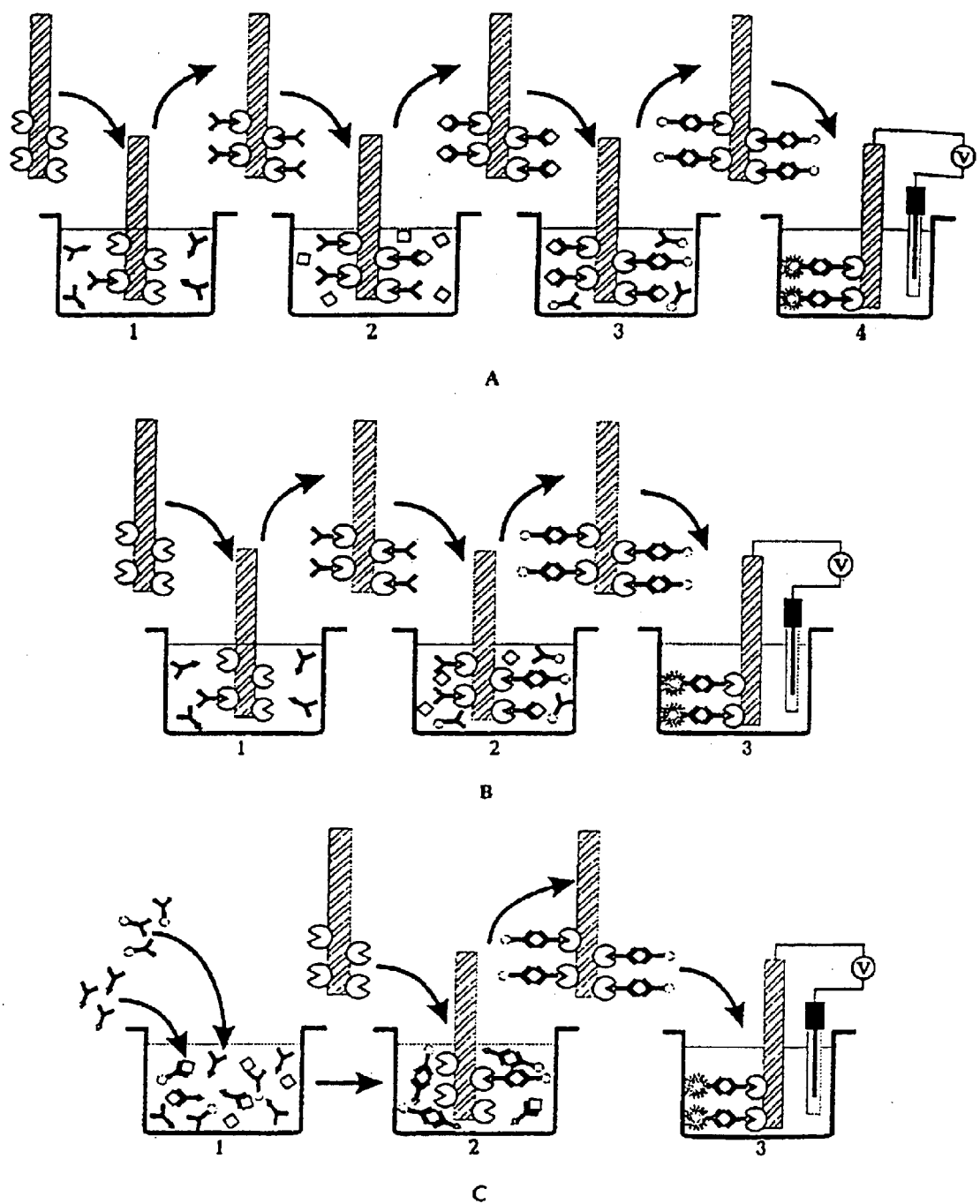

FIG. 8A: illustrates the steps of electrochemical analysis in a 'sequential' format with sequential placement of the sensing electrode in contact with a solution of biotinylated receptors [FIG. 8A1], with a test solution [FIG. 8A2], with a solution of labelled secondary receptors [FIG. 8A3], and subsequent measurement of the sensing electrode potential relative to the potential of a reference electrode [FIG. 8A4].

FIG. 8B: illustrates the steps of electrochemical analysis in which the sensing electrode is first placed in contact with a solution of biotinylated receptors [FIG. 8B1], then the sensing electrode is placed in contact with a test solution to which a solution of labelled secondary receptors has been added [FIG. 8B2], and the sensing electrode potential is then measured relative to the potential of a reference electrode [FIG. 8B3].

FIG. 8C: illustrates the steps of electrochemical analysis in a 'one-pot' format in which solutions of biotinylated receptors and labelled secondary receptors are added to a test solution [FIG. 8C1], then the sensing electrode is placed in contact with the test solution [FIG. 8C2], and the sensing electrode potential is then measured relative to the potential of a reference electrode [FIG. 8C3].

Figure 9:
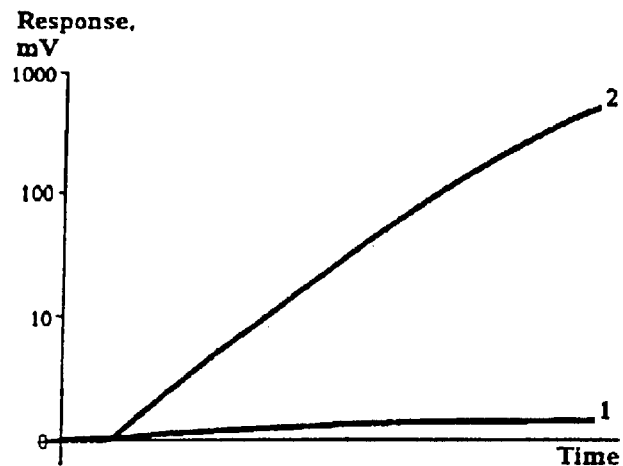

FIG. 9: illustrates the typically shape of a curve of variation in sensing electrode potential for step-wise changes in the ionic strength or composition of the working solution (on the coordinates "millivolts-time") following incubation of the sensing electrode with a test solution not containing any analyte (curve 1), and following incubation of the sensing electrode with a test solution containing analyte specific to the biotinylated receptors (curve 2).

Figure 10:
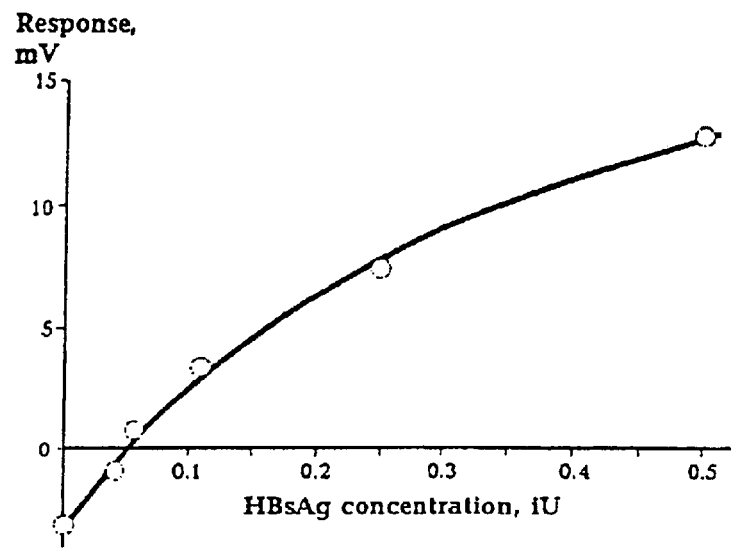

FIG. 10: shows a calibration curve of the difference in millivolts between the background and final potentials of the sensing electrode measured relative to the reference electrode versus HBsAg concentration in samples of blood serum.

Figure 11:
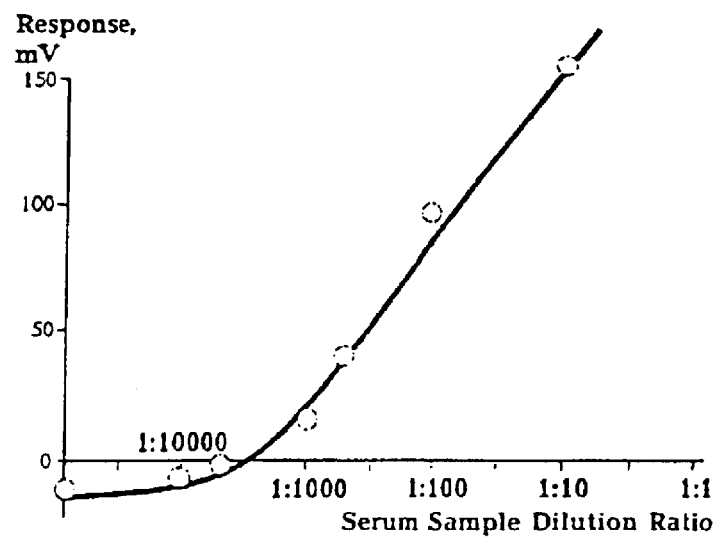

FIG. 11: shows a curve of the difference in millivolts between the background and final potentials of the sensing electrode measured relative to the reference electrode versus dilution of HBsAg-positive blood serum.

The reagents, materials and equipment used in the Examples were as follows:

Reagents and materials:

Pyrrole (>98%) was purchased from Merck and before use was purified twice by vacuum distillation, then stored under $N_2$ in an opaque vessel at +4° C.;

The following reagents were all purchased from Sigma Chemical Co. (USA): Potassium hydroxide (KOH), ACS reagent), sodium hydroxide (NaOH, ACS reagent), sodium azide (SigmaUltra), ceric sulphate (ACS reagent), potassium chloride (SigmaUltra), sodium chloride (SigmaUltra), Tris (hydroxymethyllaminomethane (SigmaUltra), sodium dodecylsulphate (SDS, >99%), sodium dextran sulphate (mol. wt. ~8000), isopropyl alcohol (ACS reagent), acetone, hydrochloric acid (ACS reagent), chloric acid (ACS reagent), N,N-dimethyl formamide (ACS reagent), glycine buffer solution 0.2M), "Tris buffered saline tablets", "Phosphate buffered saline tablets", o-Phenylenediamine dihydrochloride tablets", bovine serum albumin (RIA grade, fraction V), frozen bovine serum, streptavidin (from *Streptomyces avidinii*), NHS-d-biotin, dimethyl sulfoxide (DMSO, ACS reagent), biotin-X-X-NHS, rabbit polyclonal antibodies to bovine albumin, conjugate of goat polyclonal antibodies to mouse IgG with urease, digoxin, mouse monoclonal anti-digoxin clone DI-22 biotin conjugate, peroxidase (100 units per mg solid), disposable dialysis bags (MWCO 1,000);

Unless otherwise stated, phosphate buffered saline solution (PBS) was used throughout at pH 7.4.

Mouse monoclonal antibodies to Hepatitis B Surface Antigen (HBsAg) (5.7 mg/ml in phosphate buffered saline solution with 0.01% sodium azide), sheep polyclonal antibodies to mouse IgG (10.0 mg/ml in phosphate buffered saline solution with 0.01% sodium azide) and conjugate of mouse monoclonal antibodies to HBsAg with peroxidase (2.5 mg/ml in phosphate buffered saline solution with 0.01% sodium azide) were purchased from Sorbent-Service Ltd. (Russia);

Lyophilised insulin (bovine, ~20IU/mg) and mouse monoclonal antibodies to insulin (1.2 mg/ml in phosphate buffered saline solution), kindly contributed by members of the Cardiology Research Centre attached to the Russian Academy of Medical Sciences;

Preparation of lyophilised double-strand DNA-probe (~1 kb in length) biotinylated by nick-translation [20], preparation of lyophilised double-strand DNA complementary to biotinylated DNA-probe, preparation of lyophilised double-strand DNA non-complementary to biotinylated DNA-probe, preparation of lyophilised DNA from salmon sperm and buffer solution for DNA hybridisation, all kindly contributed by members of the Scientific Research Institute of Biophysics attached to the Ministry of Health.

Polybead® Sulphate Microspheres (2.5% Solids-Latex, 0.2 μm) were purchased from Polysciences Inc.;

Lavsan™ film (~500 μm thickness), purchased from Vladimir Chemical Plant (Russia);

Chromium target dispersed in vacuum and photoresist <<FP-383>>, purchased from NIIPIK Institute (Russia);

Deionised water (reagent grade, resistance >18 M$\Omega$) obtained using a Millipore Milli-RO/Milli-Q System;

Platinum wire, thickness ~0.5 mm;

Second British Working Standard for Hepatitis B Surface Antigen (HBsAg concentration 0.50 iU/ml), kindly contributed by the North London Blood Transfusion Centre, UK;

Samples of HBsAg-positive human sera, kindly contributed by the North London Blood Transfusion Centre, UK.

Equipment:

UVN vacuum deposition unit (Russia);

<<PNF-6Ts>> photoresist application unit (Russia);

Self-produced photo-template (a photo-template which yields the electrode design shown in FIG. 1, FIG. 3 or FIG. 4 of WO 96/02001 is suitable);

<<STP-300>> photo-exposure unit (Russia);

Self-made Soxhlet apparatus;

EU 18 dry heat cabinet (Jouan, France);

<<PI-50.1>> potentiostat-galvanostat with standard integrator and twin-coordinate recorder (Russia);

Two-channel recorder 2210 (LKB-Pribori, Sweden);

Checkmate pH meter with standard combination electrode (Mettler, Switzerland);

Self-produced Ag/AgCl semi-micro reference electrode, diameter ~2.5 mm and filled with saturated KCl solution;

Ag/AgCl reference electrode No 476370 (Corning);

Purpose designed PC-compatible measuring instrument, including amplifier and analog-to-digital converter, controlled by custom software;

Purpose designed sensing electrode and reference electrode holder.

EXAMPLE 1

HBsAg determination: competitive assay; sample-diluted specimens; receptor-biotinylated monoclonal mouse anti-HBsAg; competing molecule-labelled sheep polyclonal anti-mouse IgG; charge label-latex.

1.1. Electrode substrates were prepared from 60×48 mm Lavsan film, then washed in hot isopropanol and dried in isopropanol vapour. A 0.05 μm layer of chromium was applied to the substrates by magnetron deposition. Photoresist was applied to the chromium layer by centrifugation and dried at +80° C. for 20 minutes. The photoresist layer was exposed using ultraviolet light through a patterned photo-template. The photoresist layer was developed in KOH solution, then dried at +1000° C. for 20 minutes. The chromium pattern was obtained by etching in ceric sulphate solution. The photoresist was removed using dimethylformamide, followed by rinsing and drying in isopropanol vapour. A 0.50 μm layer of gold was applied to the chromium pattern by galvanic deposition from auric chloride solution, followed by rinsing and drying in isopropanol vapour.

1.2. The electrodes thus obtained were washed twice in 2–5% KOH solution for minutes, then rinsed with deionised water and washed twice in acetone for 5 minutes, then air dried at room temperature for 20 minutes. The electrodes were then mounted in a fluoroplastic holder and placed in a Soxhlet vessel where they were washed in hot isopropyl alcohol for 0.5–2 hours. The holder complete with electrodes was then removed from the Soxhlet vessel and the electrodes were dried in isopropyl alcohol vapour. On completion of these procedures, the electrodes were placed in a sealed glass vessel.

1.3. A storage solution for the sensing electrodes was made up by dissolving 8.0 g of sodium chloride, 12.2 g of Tris(hydroxymethyl)aminomethane, 0.2 g of potassium chloride and 0.1 g of sodium azide in 1 litre of deionised water.

1.4. Mouse monoclonal antibodies to HBsAg were biotinylated, as follows:

- 0.01M tris-saline buffered solution (pH 8.0) containing sodium azide was made by dissolving 20 tris buffered saline tablets and 0.15 g of sodium azide in 1.50 liters of deionised water;
- 1.0 mg NHS-d-biotin was dissolved in 1 ml of DMSO;
- 176 μl of the purchased mouse monoclonal antibodies to HBsAg (5.7 mg/ml) were added to a microtube containing 824 μl of 0.01M phosphate buffered saline solution;
- 50 μl of NHS-d-biotin solution in DMSO were added to the solution obtained;
- the microtube containing the mixture was placed in a thermomixer and held for 4 hours at a temperature of +22° C. with continuous mixing;
- the mixture was then dialysed at +4° C. overnight against a 500-fold excess of 0.01M tris-saline buffered solution containing sodium azide;
- the resultant solution of biotinylated antibodies was divided into aliquots of small volume (~10 μl) and stored at +4° C.

1.5. Sheep polyclonal antibodies to mouse IgG were conjugated with latex microspheres, as follows:

- a glycine buffered saline solution (pH 8.2) containing sodium azide was made up by adding 500 ml of 0.2M glycine buffer solution to 500 ml of deionised water, dissolving 8.5 g of sodium chloride and 0.1 g of sodium azide in the resultant mixture, and adjusting the pH to 8.2 with 0.1M NaOH solution;
- 60 μl of the purchased sheep polyclonal antibodies to mouse IgG (10 mg/ml) were added to a microtube containing 940 μl of glycine buffered saline solution (preferably the polyclonal antibodies are affinity purified before labelling);
- 200 μl of a 2.5% suspension of Polybead® Sulphate Microspheres were added to the resultant solution;
- the microtube containing the mixture was placed in a thermomixer and held for minutes at a temperature of 37±1° C. with continuous mixing;
- the microtube containing the mixture was then cooled to room temperature and 0.01 g of bovine serum albumin was added to it;
- the resultant solution of labelled antibodies was divided into aliquots of small volume (~5 μl) and stored at +4° C.

1.6. Prior to polymerisation, the monomer (e.g. pyrrole) is distilled in standard water cooled apparatus at atmospheric pressure at 135–140° C., and stored in a sealed opaque vessel under $N_2$ at –20° C. to –5° C. The concentration of monomer in the electrochemical polymerisation solution is varied according to the type of test within the range 0.3–1.0 M.

In this example a solution was made up for electrochemical polymerisation of pyrrole as follows:

- 2.5 ml of freshly-distilled pyrrole and 0.02 g of SDS were dissolved in 20.0 ml of deionised water;
- a phosphate-saline buffer tablet was dissolved in 200 ml of deionised water and 4.0 mg of streptavidin were dissolved in 2 ml of the PBS;
- 1 ml of streptavidin solution in PBS was added to the solution of pyrrole and SDS;
- the final solution was placed in an orbital mixer and mixed for 10 minutes.

1.7. The electrodeposition process is carried out in a triple-electrode electrochemical cell, including a working electrode, and reference electrode and an auxiliary (counter) electrode. The working electrode is a metal potentiometric electrode prepared as described above, the auxiliary electrode is a length of gold or platinum wire, and the reference is silver/silver chloride electrode.

Deposition is carried out using a potentiostat, applying a continuous voltage sweep on the working electrode. Depending on the desired thickness and properties of the polymer film, the lower potential sweep boundary, the upper potential sweep boundary, the voltage sweep rate and the number of sweep cycles are varied, typically from –500 mV to +800 mV, +1000 mV to +2000 mV (relative to the Ag/AgCl reference electrode), and 25–200 mV/sec. and 3–30 respectively.

In this example a polypyrrole film was formed by electrochemical deposition with binding of streptavidin on the electrode, as follows:

- 200 μl of electrochemical polymerisation solution were placed in a well of a microtiter plate;
- the electrode, platinum wire and semi-micro reference electrode, connected to the potentiostat, were immersed in the well;
- a cyclical sweep of the electrode potential relative to the reference electrode was applied in the range +800 to +1800 mV at a sweep rate of 150 mV/sec.;
- the process of formation of the polypyrrole film was monitored with reference to the volt-ampere curve using a twin-coordinate chart recorder connected to the corresponding outputs of the potentiostat, and with reference to the total quantity of electricity passing through the electrode using an integrator and chart recorder connected to the corresponding outputs of the potentiostat. Throughout the deposition procedure checks are made to ensure that the quantity of electricity passing through the working electrode in the first and subsequent cycles does not differ by more than 15%;
- on reaching the specified thickness of polypyrrole film (number of potential sweep cycles—8; total quantity of electricity through the electrode—750 mC), the process was stopped.

1.8. The sensing electrode coated in polypyrrole film with bound streptavidin was removed from the well, rinsed with deionised water followed by 0.01M phosphate-saline buffer solution (pH 7.4), and placed in a microtube with 300 µl of storage solution, where it was stored at +40° C.

1.9. To obtain the required quantity of sensing electrodes steps 1.7–1.8 were repeated.

1.10. A series of 200 µl samples of known HBsAg concentration were prepared in separate microtubes by diluting Second British working Standard for Hepatitis B Surface Antigen in previously thawed bovine serum with a dilution factor of 2, 4, 8 and 10, adding 100, 150, 175 and 180 µl of bovine serum to 100, 50, 25 and 20 µl of Second British Working Standard for Hepatitis B Surface Antigen, respectively. Pure bovine serum was used to provide a sample with zero HBsAg content.

1.11. 0.2 ml of a suitably titered solution of the biotinylated mouse monoclonal antibodies to HBsAg was added to 19.8 ml of 0.01M phosphate buffered saline solution, thoroughly mixed in an orbital shaker, then dispensed into microtubes in aliquots of 200 µl.

1.12. 0.1 ml of a suitably titered solution of the labelled (latex conjugated) sheep polyclonal antibodies to mouse IgG was added to 19.9 ml of 0.01 M phosphate buffered saline solution, thoroughly mixed in an orbital mixer, then dispensed into microtubes in aliquots of 200 µl.

1.13. Working buffer solution No1 was made up, as follows:

a phosphate-saline buffer tablet was dissolved in 200 ml of deionised water;

2 g of bovine serum albumin and 0.37 g of KCl were dissolved in the solution obtained.

1.14. Working buffer solution No2 was made up by dissolving a phosphate-saline buffer tablet in 200 ml of deionised water.

1.15. The appropriate number of sensing electrodes coated in polypyrrole film with bound streptavidin were removed from the storage buffer solution and each placed in one of the microtubes containing the solution of biotinylated mouse monoclonal antibodies to HBsAg (from step 1.11), and incubated for 10 minutes at room temperature.

1.16. On completion of 1.15, the sensing electrodes were removed from the microtubes containing biotinylated antibodies solution and each placed in one of the microtubes containing samples of known HBsAg concentration (from step 1.10); the microtubes with sensing electrodes were then placed in a thermomixer and held for 15 minutes at a temperature of 37±1° C., mixing continuously.

1.17. On completion of 1.16, the sensing electrodes were removed from the microtubes containing the samples and placed in the microtubes containing latex conjugated sheep polyclonal antibodies to mouse IgG (from step 1.12), then placed in a rotary shaker and held for 5 minutes at room temperature, mixing continuously.

1.18. On completion of 1.17, the sensing electrodes were removed from the microtubes, rinsed for 3–5 seconds in 0.01M phosphate buffered saline solution, and each placed in a microtiter plate well filled with working buffer solution No1.

1.19. The sensing electrode and reference electrode were connected to the electrical contacts of the holder connected to the PC-based measuring device, and the holder was positioned over the microtiter plate well filled with working buffer solution No1 such that the sensing electrode and reference electrode were immersed in the solution.

1.20. The custom software was started and used to record the sensing electrode potential in millivolts relative to the reference electrode potential for a period of 30 seconds.

1.21. On completion of 1.20, the holder was positioned over a microtiter plate well filled with working buffer solution No2, in a manner similar to that described in 1.19.

1.22. The custom software was used to record the variation in millivolts of the sensing electrode potential relative to the reference electrode potential over a period of 100 seconds.

1.23. Using the custom software, the difference $\delta$ in millivolts between the background and final potential of the sensing electrode was calculated.

1.24. The operations described in 1.19–1.21 were repeated in sequence using the samples of known HBsAg concentration prepared during step 1.10.

1.25. Based on the results obtained during step 1.24, the custom software was used to plot the curve "$\delta$ against HBsAg concentration in the sample", (FIG. 10) and the lower threshold of absolute sensitivity of the sensing electrode system was determined from this curve.

EXAMPLE 2

HBsAg determination: competitive assay; sample-diluted specimens; receptor-biotinylated monoclonal mouse anti-HBsAg; competing molecule-labelled sheep polyclonal anti-mouse IgG; charge label-latex.

2.1. The procedures described in 1.1–1.5 were carried out.

2.2. A solution was made up for electrochemical polymerisation of pyrrole, as follows:

2.5 ml of freshly-distilled pyrrole and 0.05 g of SDS were dissolved in 20.0 ml of deionised water;

2.3. A polypyrrole film was formed by electrochemical deposition, as follows:

200 µl of electrochemical polymerisation solution were placed in a well of a microtiter plate;

the electrode, platinum wire and semi-micro reference electrode, connected to the potentiostat, were immersed in the well;

a cyclical sweep of the electrode potential relative to the reference electrode was applied in the range +800 to +2200 mV at a sweep rate of 100 mV/sec.;

the process of formation of the polypyrrole film was monitored with reference to the volt-ampere curve using an X-Y chart recorder connected to the corresponding outputs of the potentiostat, and with reference to the total quantity of electricity passing through the electrode using an integrator and chart recorder connected to the corresponding outputs of the potentiostat;

on reaching the specified thickness of polypyrrole film (number of potential sweep cycles—6; total quantity of electricity through the electrode—750 mC),the process was stopped.

2.4. The sensing electrode coated in polypyrrole film was removed from the well, rinsed with deionised water followed by 0.01M phosphate-saline buffer solution (pH 7.4), and placed in a microtube with 300 µl of storage solution, where it was stored at +4° C.

2.5. To obtain the required quantity of sensing electrodes, the procedures described in 2.1–2.4 were repeated.

2.6. A solution of streptavidin was made up by dissolving a phosphate-saline buffer tablet in 200 ml of deionised water, and dissolving 1.0 mg of streptavidin in the resultant solution.

2.7. Streptavidin was bound on the surface of the polypyrrole film covering the sensing electrode, as follows:

the streptavidin solution was dispensed into microtubes in 200 µl aliquots;

the sensing electrodes coated with polypyrrole film were removed from the storage buffer solution, each placed in a microtube with streptavidin solution and incubated for 18 hours at +4° C.;

the sensing electrodes were removed from the microtubes containing streptavidin solution, washed with a 0.01M phosphate buffered saline solution and each placed in storage buffer solution, then stored at +4° C.

2.8. A series of samples with known HBsAg concentration were prepared as described in 1.10.

2.9. 0.1 ml of a suitably titered solution of the biotinylated mouse monoclonal antibodies to HBsAg was added to 19.9 ml of 0.01M phosphate buffered saline solution, thoroughly mixed in a rotary shaker, then dispensed into microtubes in aliquots of 200 $\mu$l.

2.10. 0.1 ml of a suitably titered solution of the labelled (latex conjugated) sheep polyclonal antibodies to mouse IgG was added to 19.9 ml of 0.01M phosphate buffered saline solution, thoroughly mixed in an orbital mixer, then dispensed into microtubes in aliquots of 200 $\mu$l.

2.11. Working buffer solution No1 was made up as described in 1.13.

2.12. Working buffer solution No2 was made up as described in 1.14.

2.13. The sensing electrodes coated in polypyrrole film with bound streptavidin were removed from the storage buffer solution and each placed in a microtube containing the solution of biotinylated mouse monoclonal antibodies to HBsAg (from step 2.9), and incubated for 10 minutes at room temperature.

2.14. On completion of 2.13, the sensing electrodes were removed from the microtubes containing biotinylated antibodies solution and each placed in one of the microtubes containing samples of known HBsAg concentration (from step 2.8); the microtubes with sensing electrodes were then placed in a thermomixer and held for 15 minutes at a temperature of 37±1° C., mixing continuously.

2.15. On completion of 2.14, the sensing electrodes were removed from the microtubes containing the samples and placed in the microtubes containing the solution of latex conjugated sheep polyclonal antibodies to mouse IgG (from step 2.10), then placed in a rotary shaker and held for 5 minutes at room temperature, mixing continuously.

2.16. On completion of 2.15, the sensing electrodes were removed from the microtubes, rinsed for 3–5 seconds in 0.01M phosphate buffered saline solution, and each placed in a microtiter plate well filled with working buffer solution No1.

2.17. The sensing electrode and reference electrode were connected to the electrical contacts of the holder connected to the PC-based measuring instrument, and the holder was positioned over the microtiter plate well filled with working buffer solution No1 such that the sensing electrode and reference electrode were immersed in the solution.

2.18. The custom software was started and used to record the sensing electrode potential in millivolts relative to the reference electrode potential for a period of 30 seconds.

2.19. On completion of 2.18, the holder was positioned over a microtiter plate well filled with working buffer solution No2, in a manner similar to that described in 2.17.

2.20. The custom software was used to record the variation in millivolts of the sensing electrode potential relative to the reference electrode potential over a period of 100 seconds.

2.21. Using the custom software, the difference ($\delta$) in millivolts between the background and final potential of the sensing electrode was calculated.

2.22. The operations described in 2.17–2.20 were repeated in sequence using the samples of known HBsAg concentration prepared at step 2.8.

0 2.23. Based on the results obtained at step 2.22, the custom software was used to plot the calibration curve "$\delta$ against HBsAg concentration in the sample".

2.24. A number of samples of HBsAg-positive blood serum (containing an unknown concentration of HBsAg) were each serially diluted in previously thawed bovine serum to prepare a series of samples with dilution factors of 10, 100, 1000, 5000 and 10 000. A 200 $\mu$l aliquot of each dilution was placed in a separate microtube.

2.25. The procedure described in steps 2.13–2.21 was used to determine the concentration of HBsAg in each of the dilutions and these results, together with the calibration curve obtained in step 2.23 were used to calculate the concentration of HBsAg in the original (undiluted) samples of blood serum (FIG. 11).

EXAMPLE 3

Anti-albumin antibody determination: competitive assay; sample-rabbit polyclonal antibodies against albumin; receptor-biotinylated bovine serum albumin; competing molecule-labelled rabbit polyclonal antibodies to albumin; charge label-latex.

3.1. The procedures described in 1.1–1.3 were carried out.

3.2. Bovine serum albumin (BSA) was biotinylated as described in 1.4. The resultant solution of biotinylated BSA was divided into aliquots of small volume (~10 $\mu$l) and stored at +4° C.

3.3. Rabbit polyclonal antibodies to bovine albumin were conjugated with latex microspheres following the procedure described in 1.5. The resultant solution of labelled antibodies was divided into aliquots of small volume (~$\mu$l) and stored at +4° C.

3.4. A solution was made up for electrochemical polymerisation of pyrrole, as described in 2.2.

3.5. A polypyrrole film was formed by electrochemical deposition, as described in 2.3.

3.6. The sensing electrode coated in polypyrrole film was removed from the well, rinsed with deionised water followed by 0.01M phosphate-saline buffer solution (pH 7.4), and placed in a microtube with 300 $\mu$l of storage solution, where it was stored at +4° C.

3.7. To obtain the required quantity of sensing electrodes, the procedures described in 3.1–3.6 were repeated.

3.8. A solution of streptavidin was made up as described in 2.6.

3.9. Streptavidin was bound on the surface of the polypyrrole film covering the sensing electrode, as described in 2.7.

3.10. A series of samples with known concentration of unlabelled rabbit polyclonal antibodies to bovine albumin were prepared, as follows:

the purchased sample of rabbit polyclonal antibodies to bovine albumin was dialysed at +4° C. overnight against a 500-fold excess of 0.01M phosphate buffered saline solution;

the resultant solution of rabbit polyclonal antibodies to bovine albumin in 0.01M phosphate buffered saline solution was serially diluted with 0.01M phosphate buffered saline solution at dilution factors of 10, 20, 50, 100, 1000 and 5000;

200 $\mu$l aliquots of each of the diluted samples were placed in separate microtubes.

3.11. 0.8 ml of a suitably diluted solution of biotinylated BSA was added to 19.2 ml of 0.01M phosphate buffered saline solution, thoroughly mixed in a rotary shaker, then dispensed into microtubes in aliquots of 200 $\mu$l.

3.12. 0.1 ml of a suitably titered solution of labelled (latex conjugated, as described above) rabbit polyclonal antibodies to bovine albumin was added to 19.9 ml of 0.01M phosphate buffered saline solution, thoroughly mixed in an orbital mixer, then dispensed into microtubes in aliquots of 200 $\mu$l.

3.13. Working buffer solution No1 was made up, as follows:
   a phosphate-saline buffer tablet was dissolved in 200 ml of deionised water;
   0.37 g of KCl were dissolved in the solution obtained.
3.14. Working buffer solution No2 was made up as described in 1.14.
3.15. The sensing electrodes coated in polypyrrole film with bound streptavidin were removed from the storage buffer solution and each placed in one of the microtubes containing 200 μl of biotinylated BSA solution (from step 3.11), and incubated for 25 minutes at room temperature.
3.16. On completion of 3.15, the sensing electrodes were removed from the microtubes containing biotinylated BSA solution and each placed in one of the microtubes containing samples with known concentration of unlabelled rabbit polyclonal antibodies to bovine albumin (from step 3.10); the microtubes with sensing electrodes were then placed in a thermomixer and held for minutes at a temperature of 37±1° C., mixing continuously.
3.17. On completion of 3.16, the sensing electrodes were removed from the microtubes containing the samples and transferred to microtubes containing the solution of latex conjugated rabbit polyclonal antibodies to bovine albumin (from step 3.12), then placed in a rotary shaker and held for 10 minutes at room temperature, mixing continuously.
3.18. On completion of 3.17, the sensing electrodes were removed from the microtubes, rinsed for 3–5 seconds in 0.01M phosphate buffered saline solution, and each placed in a microtiter plate well filled with working buffer solution No1.
3.19. The sensing electrode and reference electrode were connected to the electrical contacts of the holder connected to the PC-based measuring instrument, and the holder was positioned over the microtiter plate well filled with working buffer w solution No1 such that the sensing electrode and reference electrode were immersed in the solution.
3.20. The custom software was started and used to record the sensing electrode potential in millivolts relative to the reference electrode potential over a period of 100 seconds.
3.21. On completion of 3.20, the holder was positioned over a microtiter plate well filled with working buffer solution No2, in a manner similar to that described in 3.19.
3.22. The custom software was used to record the variation in millivolts of the sensing electrode potential relative to the reference electrode potential over a period of 200 seconds.
3.23. Using the custom software, the area (integral) $S_2$ described by the curve of sensing electrode potential variation versus reference electrode potential was calculated.
3.24. The operations described in 3.19–3.23 were repeated in sequence using the samples with known concentration of unlabelled rabbit polyclonal antibodies to bovine albumin prepared at step 3.10.
3.25. Based on the results obtained at step 3.24, the custom software was used to plot the calibration curve "$S_2$ against concentration of unlabelled rabbit polyclonal antibodies to bovine albumin in the sample".

EXAMPLE 4

HBsAg determination; sandwich assay; sample-sample with known HBsAg concentration; receptor-biotinylated mouse monoclonal antibodies to HBsAg; labelled mouse monoclonal antibodies to HBsAg; label-peroxidase.

4.1. The procedures described in 1.1–1.4 were carried out.
4.2. A solution was made up for electrochemical polymerisation of pyrrole, as described in 2.2.
4.3. A polypyrrole film was formed by electrochemical deposition, as described in 2.3.
4.4. The sensing electrode coated in polypyrrole film was removed from the well, rinsed with deionised water followed by 0.01M phosphate-saline buffer solution (pH 7.4), and placed in a microtube with 300 μl of storage solution, where it was stored at +4° C.
4.5. To obtain the required quantity of sensing electrodes, the procedures described in 4.1–4.4 were repeated.
4.6. A solution of streptavidin was made up as described in 2.6.
4.7. Streptavidin was bound on the surface of the polypyrrole film covering the sensing electrode, as described in 2.7.
4.8. A series of samples with known HBsAg concentration were prepared, as described in 1.10.
4.9. 0.2 ml of a suitably titered solution of the biotinylated mouse monoclonal antibodies to HBsAg was added to 19.8 ml of 0.01M phosphate buffered saline solution, thoroughly mixed in a rotary shaker, then dispensed into microtubes in aliquots of 200 μl.
4.10. 5 ml of previously thawed bovine serum were added to 15 ml of 0.01M phosphate buffered saline solution, and 0.4 ml of a suitably titered solution of purchased peroxidise conjugated mouse monoclonal antibodies to HBsAg was added to 19.6 ml of the resultant solution, which was then thoroughly mixed in a rotary shaker and dispensed into microtubes in aliquots of 200 μl.
4.11. Working buffer solution No1 was made up by dissolving a phosphate-saline buffer tablet in 200 ml of deionised water.
4.12. Working buffer solution No2 was made up, as follows:
   an o-Phenylenediamine dihydrochloride tablet and a urea hydrogen peroxide/buffer tablet were dissolved in 20 ml of deionised water;
   0.1 ml of the solution obtained was added to 19.9 ml of 0.01M phosphate buffered saline solution, thoroughly mixed in a rotary shaker, then placed in an opaque glass vessel and stored at +4° C. until the start of the test.
4.13. The sensing electrodes coated in polypyrrole film with bound streptavidin were removed from the storage buffer solution and each placed in a microtube containing 200 μl of the solution of biotinylated mouse monoclonal antibodies to HBsAg (from step 4.9) and incubated for 5 minutes at room temperature.
4.14. On completion of 4.13, the sensing electrodes were removed from the microtubes containing biotinylated antibodies solution and placed in microtubes containing samples with known HBsAg concentration (from step 4.8); the microtubes with sensing electrodes were then placed in a thermomixer and held for 10 minutes at a temperature of 37±1° C., mixing continuously.
4.15. On completion of 4.14, the sensing electrodes were removed from the microtubes containing the samples and placed in microtubes containing the solution of peroxidase-conjugated mouse monoclonal antibodies to HBsAg (from step 4.10), then placed in a rotary shaker and held for 5 minutes at room temperature, mixing continuously.
4.16. On completion of 4.15, the sensing electrodes were removed from the microtubes, rinsed for 3–5 seconds in 0.01M phosphate buffered saline solution, and each placed in a microtiter plate well filled with working buffer solution No1.
4.17. The sensing electrode and reference electrode were connected to the electrical contacts of the holder connected to the PC-based measuring instrument, and the holder was positioned over the microtiter plate well filled with working buffer solution No1 such that the sensing electrode and reference electrode were immersed in the solution.

4.18. The custom software was started and used to record the sensing electrode potential in millivolts relative to the reference electrode potential over a period of 50 seconds.

4.19.. On completion of 4.18, the holder was positioned over a microtiter plate well filled with working buffer solution No2, in a manner similar to that described in 4.17.

4.20. The custom software was used to record the variation in millivolts of the sensing electrode potential relative to the reference electrode potential over a period of 100 seconds.

4.21. Using the custom software, the difference ($\delta$) in millivolts between the background and final potential of the sensing electrode was calculated.

4.22. The operations described in 4.17–4.21 were repeated in sequence using the samples of known HBsAg concentration prepared at step 4.8.

4.23. Based on the results obtained at step 4.22, the custom software was used to plot the calibration curve "$\delta$ against HBsAg concentration in the sample".

4.24. A series of diluted blood serum samples were prepared as described in 2.24.

4.25. The procedure described in steps 4.13–4.21 was used to determine the concentration of HBsAg in each of the diluted samples prepared in 4.24 and these results, together with the calibration curve obtained in step 4.23 were used to calculate the concentration of HBsAg in the original (undiluted) samples of blood serum.

EXAMPLE 5

HBsAg determination; sandwich assay; sample-sample with known HBsAg concentration; receptor-biotinylated mouse monoclonal antibodies to HBsAg; labelled mouse monoclonal antibodies to HBsAg; label-peroxidase; "sequential assay".

5.1. The procedures described in 1.1–1.4 were carried out.

5.2. A solution was made up for electrochemical polymerisation of pyrrole, as described in 2.2.

5.3. A polypyrrole film was formed by electrochemical deposition, as described in 2.3.

5.4. The sensing electrode coated in polypyrrole film was removed from the well, rinsed with deionised water followed by 0.01M phosphate-saline buffer solution (pH 7.4), and placed in a microtube with 300 µl of storage solution, where it was stored at +4° C.

5.5. To obtain the required quantity of sensing electrodes, the procedures described in 5.1–5.4 were repeated.

5.6. A solution of streptavidin was made up as described in 2.6.

5.7. Streptavidin was bound on the surface of the polypyrrole film covering the sensing electrode, as described in 2.7.

5.8. A series of samples with known HBsAg concentration were prepared, as described in 1.10.

5.9. 0.5 ml of a solution of biotinylated mouse monoclonal antibodies to HBsAg was added to 19.5 ml of 0.01M phosphate buffered saline solution, thoroughly mixed in a rotary shaker, then dispensed into microtubes in aliquots of 200 µl.

5.10. 1.7 ml of a solution of peroxidase-labelled mouse monoclonal antibodies to HBsAg was added to 18.3 ml of 0.01M phosphate buffered saline solution, thoroughly mixed in an orbital mixer and dispensed into microtubes in aliquots of 200 µl.

5.11. Working buffer solution No1 was made up as described in 4.11.

5.12. Working buffer solution No2 was made up as described in 4.12.

5.13. The sensing electrodes coated in polypyrrole film with bound streptavidin were removed from the storage buffer solution and each placed in a microtube containing the solution of biotinylated mouse monoclonal antibodies to HBsAg (from step 5.9), and incubated for minutes at room temperature.

5.14. Simultaneously with step 5.13, 10 µl of a suitably titered solution of the purchased peroxidase-labelled mouse monoclonal antibodies to HBsAg were added to each sample with known HBsAg concentration (from step 5.8), having first removed 10 µl from the sample; the microtubes and samples were then placed in a thermomixer at 37±1° C. for 5–10 minutes.

5.15. On completion of 5.13–5.14, the sensing electrodes were removed from the microtubes containing the solution of biotinylated antibodies and placed in the microtubes containing samples with known HBsAg concentration (from step 5.14) then held in the thermomixer for 15 minutes at 37±1° C., mixing continuously.

5.16. On completion of 5.15, the sensing electrodes were removed from the microtubes, rinsed for 3–5 seconds in 0.01M phosphate buffered saline solution, and each placed in a microtiter plate well filled with working buffer solution No1.

5.17. The sensing electrode and reference electrode were connected to the electrical contacts of the holder connected to the PC-based measuring instrument, and the holder was positioned over the microtiter plate well filled with working buffer solution No1 such that the sensing electrode and reference electrode were immersed in the solution.

5.18. The custom software was started and used to record the sensing electrode potential in millivolts relative to the reference electrode potential over a period of 50 seconds.

5.19. On completion of 5.18, the holder was positioned over a microtiter plate well filled with working buffer solution No2, in a manner similar to that described in 5.17.

5.20. The custom software was used to record the variation in millivolts of the sensing electrode potential relative to the reference electrode potential over a period of 200 seconds.

5.21. Using the custom software, the area (integral) $S_2$ described by the curve of sensing electrode potential variation versus reference electrode potential was calculated.

5.22. The operations described in 5.17–5.21 were repeated in sequence using the samples with known HBsAg concentration prepared at step 5.8.

5.23. Based on the results obtained at step 5.22, the custom software was used to plot the calibration curve "$S_2$ against HBsAg concentration in the sample".

5.24. A series of diluted blood serum samples were prepared as described in 2.24.

5.25. The procedure described in steps 5.13–5.21 was used to determine the concentration of HBsAg in each of the diluted samples prepared in 5.24 and these results, together with the calibration curve obtained in step 5.23, were used to calculate the concentration of HBsAg in the original (undiluted) samples of blood serum.

EXAMPLE 6

HBsAg determination; sandwich assay; sample-sample with known HBsAg concentration; receptor-biotinylated mouse monoclonal antibodies to HBsAg; labelled mouse monoclonal antibodies to HBsAg; label-peroxidase; "one-pot assay".

6.1 The procedures described in 1.1–1.4 were carried out.

6.2. A solution was made up for electrochemical polymerisation of pyrrole, as described in 2.2.

6.3. A polypyrrole film was formed by electrochemical deposition, as described in 2.3.

6.4. The sensing electrode coated in polypyrrole film was removed from the well, rinsed with deionised water followed by 0.01M phosphate-saline buffer solution (pH 7.4), and placed in a microtube with 300 µl of storage solution, where it was stored at +4° C.

6.5. To obtain the required quantity of sensing electrodes, the procedures described in 6.1–6.4 were repeated.

6.6. A solution of streptavidin was made up as described in 2.6.

6.7. Streptavidin was bound on the surface of the polypyrrole film covering the sensing electrode, as described in 2.7.

6.8. A series of samples with known HBsAg concentration were prepared, as described in 1.10.

6.9. 2.5 ml of a suitably titered solution of the biotinylated mouse monoclonal antibodies to HBsAg was added to 17.5 ml of 0.01M phosphate buffered saline solution, thoroughly mixed in a rotary shaker, then dispensed into microtubes in aliquots of 200 µl.

6.10. 1.7 ml of a suitably titered solution of the purchased peroxidase-labelled mouse monoclonal antibodies to HBsAg was added to 18.3 ml of 0.01M phosphate buffered saline solution, thoroughly mixed in a rotary shaker and dispensed into microtubes in aliquots of 200 µl.

6.11. Working buffer solution No1 was made up as described in 4.11.

6.12. Working buffer solution No2 was made up as described in 4.12.

6.13. 10 µl of a solution of biotinylated mouse monoclonal antibodies to HBsAg (from step 6.9) and 10 µl of peroxidase-labelled mouse monoclonal antibodies to HBsAg (from step 6.10) were added to each sample of known HBsAg concentration, having first removed 20 µl from the sample; the microtubes and samples were then placed in a thermomixer, where they were incubated for minutes at 37±1° C., mixing continuously.

6.14. On completion of 6.13, the sensing electrodes coated in polypyrrole film with bound streptavidin were removed from the storage buffer solution, each placed in the microtubes containing samples with known HBsAg concentration (from step 6.13), then held in the thermomixer for 5 minutes at a temperature of 37±1° C., mixing continuously.

6.15. On completion of 6.14, the sensing electrodes were removed from the microtubes, rinsed for 3–5 seconds in 0.01M phosphate buffered saline solution, and each placed in a microtiter plate well filled with working buffer solution No1.

6.16. The sensing electrode and reference electrode were connected to the electrical contacts of the holder connected to the PC-based measuring instrument, and the holder was positioned over the microtiter plate well filled with working buffer solution No1 such that the sensing electrode and reference electrode were immersed in the solution.

6.17. The custom software was started and used to record the sensing electrode potential in millivolts relative to the reference electrode potential over a period of 100 seconds.

6.18. On completion of 6.17, the holder was positioned over a microtiter plate well filled with working buffer solution No2, in a manner similar to that described in 6.16.

6.19. The custom software was used to record the variation in millivolts of the sensing electrode potential relative to the reference electrode potential over a period of 200 seconds.

6.20. Using the custom software, the area (integral) $S_2$ described by the curve of sensing electrode potential variation versus reference electrode potential was calculated.

6.21. The operations described in 6.16–6.20 were repeated in sequence using the samples with known HBsAg concentration prepared at step 6.8.

6.22. Based on the results obtained at step 6.21, the custom software was used to plot the calibration curve "$S_2$—RBsAg concentration in the sample".

6.23. A series of diluted blood serum samples were prepared as described in 2.24.

6.24. The procedure described in steps 6.13–6.21 was used to determine the concentration of HBsAg in each of the diluted samples prepared in 6.23 and these results, together with the calibration curve obtained in step 6.22, were used to calculate the concentration of HBsAg in the original (undiluted) samples of blood serum.

EXAMPLE 7

Insulin determination; competitive assay; sample-samples with known insulin conc; receptor-biotinylated mouse monoclonal antibodies to insulin; competing molecule-labelled polyclonal goat anti-mouse IgG antibodies; label-urease 7.1. The procedures described in 1.1–1.3 were carried out.

7.2. Biotinylation of mouse monoclonal antibodies to insulin was carried out as described in 1.4. The resultant solution of biotinylated mouse monoclonal antibodies to insulin was divided into aliquots of small volume (~10 µl) and stored at +4° C.

7.3. A solution was made up for electrochemical polymerisation of pyrrole, as described in 2.2.

7.4. A polypyrrole film was formed by electrochemical deposition, as described in 2.3.

7.5. The sensing electrode coated in polypyrrole film was removed from the well, rinsed with deionised water followed by 0.01M phosphate-saline buffer solution (pH 7.4), and placed in a microtube with 300 µl of storage solution, where it was stored at +4° C.

7.6. To obtain the required quantity of sensing electrodes, the procedures described in 7.4–7.5 were repeated.

7.7. A solution of streptavidin was made up as described in 2.6.

7.8. Streptavidin was bound on the surface of the polypyrrole film covering the sensing electrode, as described in 2.7.

7.9. A series of samples with known insulin concentration were prepared, as follows:

1.12 g of potassium chloride and 1.0 g of bovine serum albumin were dissolved in 100 ml of deionised water;

100 µg of lyophilised insulin were dissolved in 200 µl of the solution obtained;

the insulin solution obtained was sequentially diluted with deionised water with potassium chloride and bovine serum albumin at dilution factors of 10, 20, 50, 100, 1000, 5000 and 10,000 times;

200 µl aliquots of each of the diluted samples were placed in separate microtubes.

7.10. 0.8 ml of a suitably titered solution of the biotinylated mouse monoclonal antibodies to insulin were added to 19.2 ml of 0.01M phosphate buffered saline solution, throughly mixed in a rotary shaker, then aliquotted into microtubes in quantities of 200 µl.

7.11. 0.02 ml of purchased urease conjugated goat polyclonal antibodies to mouse IgG was added to 19.98 ml of 0.01M phosphate buffered saline solution, throughly mixed in a rotary shaker and aliquotted into microtubes in quantities of 200 µl.

7.12. Working buffer solution No1 was made up by dissolving 2.24 g of potassium chloride in 200 ml of deionised water.

7.13. Working buffer solution No2 was made up by dissolving 0.012 g of urea in 20 ml of working buffer solution No1.

7.14. The sensing electrodes coated in polypyrrole film with bound streptavidin were removed from the storage solution, each placed in a microtube with the solution of biotinylated mouse monoclonal antibodies to insulin (from step 7.10), and incubated for 10 minutes.

7.15. On completion of 7.14, the sensing electrodes were removed from the microtubes with the solution of biotinylated antibodies and placed in microtubes containing samples of known insulin concentration (from step 7.9), then placed in a thermomixer and held for 15 minutes at a temperature of 37±1° C., mixing continuously.

7.16. On completion of 7.15, the sensing electrodes were removed from the microtubes containing the samples and placed in microtubes containing the solution of urease conjugated goat polyclonal antibodies to mouse IgG (from step 7.11), then placed in a rotary shaker and held for 10 minutes at room temperature, mixing continuously.

7.17. On completion of 7.16, the sensing electrodes were removed from the microtubes, rinsed for 3–5 seconds in deionised water with potassium chloride and bovine serum albumin, and each placed in microtiter plate well filled with working buffer No1.

7.18. The sensing electrode and reference electrode were connected to the electrical contacts of the holder connected to the PC-based measuring device, and the holder was positioned over the microtiter plate well filled with working buffer solution No1 such that the sensing electrode and reference electrode were immersed in the solution.

7.19. The custom software was started and used to record the sensing electrode potential in millivolts relative to the reference electrode potential over a period of 200 seconds.

7.20. On completion of 7.19, the holder was positioned over a microtiter plate well filled with working buffer solution No2, in a manner similar to that described in 7.18.

7.21. The custom software was used to record the variation in millivolts of the sensing electrode potential relative to the reference electrode potential over a period of 400 seconds.

7.22. Using the custom software, the area (integral) $S_2$ described by the curve of sensing electrode potential variation versus reference electrode potential was calculated.

7.23. The operations described in 7.18–7.22 were repeated in sequence using the samples with known insulin concentration prepared at step 7.9.

7.24. Based on the results obtained at step 7.23, the custom software was us ed to plot the calibration curve "$S_2$ against insulin concentration in the sample".

EXAMPLE 8

Nucleic acid hybridisation.

8.1. The procedures described in 1.1–1.3 were carried out.

8.2. A solution was made up for electrochemical polymerisation of pyrrole, as described in 2.2.

8.3 A polypyrrole film was formed by electrochemical deposition , as described in 2.3.

8.4. The sensing electrode coated in polypyrrole film was removed from the well, rinsed with deionised water followed by 0.01 M phosphate saline buffer solution (pH 7.4), and placed in a microtube with 300 µl of storage solution, where it was stored at +4° C.

8.5. To obtain the required quantity of sensing electrodes, the procedures described in 8.3–8.4 were repeated.

8.6. A solution of streptavidin was made up by dissolving a phosphate buffered saline tablet in 200 ml of deionised water and dissolving 5.0 mg of streptavidin in the solution obtained.

8.7. Streptavidin was bound on the surface of the polypyrrole film covering the sensing electrode, as follows:

the streptavidin solution was dispensed into microtubes in aliquots of 300 µl;

the sensing electrodes coated with polypyrrole film were removed from the storage solution, each placed in a microtube containing streptavidin solution and incubated for 24 hours at +4° C.;

the sensing electrodes were removed from the microtubes containing streptavidin solution, rinsed with 0.01M phosphate buffered saline solution and twice with deionised water containing 0.01% sodium azide and 0.15M potassium chloride: each sensing electrode was then placed in storage solution and stored at +4° C.

8.8 A solution of biotinylated single-strand DNA probe was prepared, as follows:

1 mg of lyophilised preparation of biotinylated double strand DNA probe (~1 kb in length) was dissolved in 1 ml of deionised water, and the solution obtained was placed in a microtube.

the microtube containing the DNA probe solution was placed in a water bath where it was incubated for 5–8 minutes at +100° C.;

the microtube containing the DNA probe was transferred to a vessel containing ice, where it was rapidly cooled to 0° C.;

the microtube containing the DNA probe was then transferred to a freezer where it was stored frozen at −20° C.

8.9. A solution of single-strand DNA complementary to biotinylated DNA-probe was prepared, as follows:

10 mg of lyophilised preparation of double-strand DNA complementary to biotinylated DNA -probe was dissolved in 1 ml of deionised water, and the solution obtained was placed in a microtube;

the microtube containing the DNA solution was placed in a water bath, where it was incubated for 5–8 minutes at +100° C.;

the microtube containing the DNA solution was transferred to a vessel containing ice, where it was rapidly cooled to 0° C.;

the microtube containing the DNA solution was then transferred to a freezer where it was stored frozen at −20° C.

8.10. A solution of single-strand DNA non-complementary to biotinylated DNA probe was prepared as described in 8.9.

8.11 Working buffer solution No1 was made up as follows:
- a phosphate buffered saline tablet was dissolved in 200 ml of deionised water;
- 2 g of bovine serum albumin, 0.37 g of potassium chloride and 0.12 g of sodium citrate were dissolved in the solution obtained.

8.12. Working buffer solution No2 was made up as follows:
- a phosphate buffered saline tablet was dissolved in 200 ml of deionised water;
- 2 g of bovine serum albumin and 1 g of sodium dextran sulphate were dissolved in the solution obtained.

8.13. The sensing electrodes coated in polypyrrole film with bound streptavidin were removed from the deionised water containing 0.01% sodium azide and 0.15M potassium chloride, and 20 µl of single-strand DNA probe solution previously thawed and warmed to room temperature was applied to working the surface of each sensing electrode.

8.14. On completion of 8.13, the sensing electrodes were placed in a humidity chamber where they were incubated for 60 minutes at +44° C.

8.15. On completion of 8.14, the sensing electrodes were removed from the humidity chamber and each placed in a microtube containing 200 µl of initial buffer solution for DNA hybridisation, where they were held for a short period of time at +4° C. (The DNA hybridisation buffer may be any standard hybridisation buffer known in the art, see Sambrook, J., Fritsch, E. F. and Maniatis, T. (1989) *Molecular Cloning: A Laboratory Manual*, 2nd Edition, Cold Spring Harbor Laboratory Press, Cold Spring Harbor, N.Y., USA)

8.16. Samples containing single-strand DNA complementary to biotinylated DNA probe were prepared, as follows:
- 10 mg of a preparation of lyophilised DNA from salmon sperm was dissolved in 10 ml of initial buffer solution for DNA hybridisation.
- 10 µl of the solution of single-strand DNA complementary to biotinylated DNA-probe previously thawed and warmed to room temperature were added to 0.99 ml of the solution obtained:
- the resulting solution was thoroughly mixed in a rotary shaker and dispensed into microtubes aliquots of 200 µl.

8.17. Samples containing single-strand DNA non-complementary to biotinylated DNA probe were prepared, as follows:
- 10 mg of a preparation of lyophilised DNA from salmon sperm was dissolved in 10 ml of initial buffer solution for DNA hybridisation;
- 100 µl of the solution of single-strand DNA non-complementary to biotinylated DNA probe previously thawed and warmed to room temperature were added to 0.9 ml of the solution obtained;
- the resulting solution was throughly mixed in a rotary shaker and dispensed into microtubes in aliquots of 200 µl.

8.18. Half of the sensing electrodes with immobilised biotinylated single-strand DNA-probe were removed from the microtubes containing initial buffer solution for DNA hybridisation and placed in the microtubes with samples containing DNA complementary to biotinylated DNA-probe; the microtubes containing the sensing electrodes were then placed in a thermomixer and held for 120 minutes at +42° C. mixing continuously.

8.19. On completion of 8.18, the sensing electrodes were removed from the microtubes, rinsed for 3–5 seconds in working buffer solution No1 and each placed in the well of a microtiter plate filled with working buffer solution No1.

8.20. The sensing electrode and reference electrode were connected to the electrical contacts of the holder connected to the PC-based measuring device, and the holder was positioned over the microtiter plate well filled with working buffer solution No1 such that the sensing electrode and reference electrode were immersed in the solution.

8.21. The custom software was started and used to record the sensing electrode potential in millivolts relative to the reference electrode potential over a period of 200 seconds.

8.22. On completion of 8.21, the holder was positioned over a microtiter plate well filled with working buffer solution No2, in a manner similar to that described in 8.20.

8.23. The custom software was used to record the variation in millivolts of the sensing electrode potential relative to the reference electrode potential over a period of 600 seconds.

8.24. Using the custom software, the difference ($\delta$) in millivolts between the background and final potential values was calculated.

8.25. The operations described in 8.20–8.24 were repeated in sequence using the samples containing DNA complementary to biotinylated DNA probe prepared at step 4.8.

8.26. The other half of the sensing electrodes with immobilised biotinylated single-strand DNA probe were removed from the microtubes containing initial buffer solution for DNA hybridisation and placed in the microtubes with samples containing DNA non-complementary to DNA probe, the microtubes containing the sensing electrode were then placed in a thermomixer and held for 120 minutes at +42° C., mixing continuously.

8.27. The procedures described in 8.19–8.25 were repeated using the samples containing DNA non-complementary to biotinylated DNA probe.

8.28. Based on the results obtained in 8.19–8.26, the custom software was used to plot statistical distribution curves of the $\delta$ values obtained with the samples of DNA complementary and non-complementary to biotinylated DNA probe.

EXAMPLE 9

Digoxin determination; competitive assay; samples—samples with known digoxin concentration; receptor-biotinylated mouse monoclonal antibodies to digoxin; competing molecule-labelled digoxin; label-peroxidase.

9.1 The procedures described in 1.1–1.4 were carried out.

9.2 A solution was made up for electrochemical polymerisation of pyrrole, as described in 2.2.

9.3 A polypyrrole film was formed by electrochemical deposition, as described in 2.3.

9.4 The sensing electrode coated in polypyrrole film was removed from the well, rinsed with deionised water followed by 0.01M phosphate-saline buffer solution (pH 7.4) and placed in a microtube with 300 µl of storage solution, where it was stored at +4° C.

9.5 To obtain the required number of sensing electrodes, the procedures described in 9.1–9.4 were repeated.

9.6 A solution of streptavidin was made up as described in 2.6.

9.7 Streptavidin was bound on the surface of the polypyrrole film covering the sensing electrode, as described in 2.7.

9.8 A series of samples with known digoxin concentration were prepared as follows:
- 250 ml of ethanol were added to 750 ml of deionised water;
- 250mg of digoxin were dissolved in 1000 ml of the ethanol solution obtained;
- a phosphate saline buffer tablet and 10.0 g of bovine serum albumin were dissolved in 200 ml of deionised water;
- the digoxin solution obtained was sequentially diluted in PBS solution with bovine serum albumin at dilution rates of 250, 2500, 25000, 50000, 125000, 250000 and 500000 times;
- 200 µl aliquots of each of the diluted samples were placed in separate microtubes.

9.9 20 µl of the purchased solution of biotin conjugated mouse monoclonal antibodies to digoxin were added to 19.98 ml of 0.01M phosphate buffered solution (pH 7.4), thoroughly mixed in a rotary shaker, then aliquotted into microtubes in quantities of 200 µl.

9.10 Digoxin was conjugated with peroxidase according to a previously described protocol, see [21]. The resultant solution of peroxidase labelled digoxin (final concentration ~0.1 mg/ml) was diluted with 0.01M phosphate saline buffer solution (pH 7.4) at a dilution ratio of 10 times then divided into aliquots of small volume (10 µl) and stored at +4° C.

9.11 Working buffer solution No1 was made up as described in 4.11.

9.12 Working buffer solution N2 was made up as described in 4.12.

9.13 The sensing electrodes coated in polypyrrole film with bound streptavidin were removed from the storage buffer solution and each placed in a microtube containing the solution of biotin conjugated mouse monoclonal antibodies to digoxin (from step 9.9) and incubated for 10 minutes at room temperature.

9.14 Simultaneously with step 9.13, 2 µl of the solution of peroxidase labelled digoxin (from step 9.10) was added to each of the samples with known digoxin concentration (from step 9.8), having first removed 2 µl from the sample.

9.15 On completion of steps 9.13 and 9.14, the sensing electrodes were transferred to the tubes containing peroxidase labelled and unlabelled digoxin (from step 9.14); the tubes plus sensing electrodes were then placed in a thermomixer and held for 10 minutes at 37±1° C., mixing continuously.

9.16 On completion of 9.15, the sensing electrodes were removed from the microtubes, rinsed for 3–5 seconds in 0.01M PBS and each placed in a microtiter plate well filled with working buffer solution No1.

9.17 The sensing electrode and reference electrode were connected to the electrical contacts of the holder connected to the Pc-based measuring instrument, and the holder was positioned over the microtiter plate well filled with working buffer solution No1 such that the sensing electrode and reference electrode were immersed in the working buffer.

9.18 the custom software was started and used to record the sensing electrode potential in millivolts relative to the reference electrode potential over a period of 30 seconds.

9.19 on completion of 9.18, the holder was positioned over a microtiter plate well filled with working buffer solution No2, in a manner similar to that described in 9.17.

9.20 the custom software was used to record the variation in millivolts of the sensing electrode potential relative to the reference electrode potential over a period of 100 seconds.

9.21 using the custom software, the area (integral) $S_2$ described by the curve of sensing electrode potential variation versus reference electrode potential was calculated.

9.22 the operations described in 9.17–9.21 were repeated in sequence using the samples with known digoxin concentration prepared at step 9.8.

9.23 based on the results obtained at step 9.22, the custom software was used to plot the calibration curve "$S_2$ against digoxin concentration in the sample".

What is claimed is:

1. A method of electrochemical detection of an analyte in a sample, which method comprises the steps of:
   (a) providing a sensing electrode having an electroconductive polymer coating, the coating having immobilised therein or adsorbed thereto receptors which are capable of binding the desired analyte to be detected in the sample;
   (b) contacting the sensing electrode with a test solution comprising the sample so that the desired analyte to be detected in the sample binds to said immobilised or adsorbed receptors;
   (c) contacting the sensing electrode with a solution comprising secondary receptors capable of binding to said analyte at a site spatially distinct from the site of binding to the immobilised or adsorbed receptors, said secondary receptors being conjugated with a charge label;
   (d) monitoring the electric potential difference between the sensing electrode of part (c) and a reference electrode when both are immersed in an electrolyte; and
   (e) monitoring the electric potential difference between the sensing electrode of part (d) and a reference electrode following a change in the ionic strength of the electrolyte at constant pH.

2. A method as claimed in claim 1 wherein the charge label has the following properties:
   (i) it carries a net charge at the pH of the electrolyte of part d); and
   (ii) the magnitude of this charge changes in response to a change in the ionic strength of the electrolyte at constant pH.

3. A method as claimed in claim 2 wherein the charge label is ferrocene, latex microspheres or gold.

4. A method as claimed in claim 1 wherein the charge label has a net charge at the pH of the electrolyte of greater than one electrostatic unit.

5. A method as claimed in claim 1 wherein steps (b) and (c) are performed simultaneously by contacting the sensing electrode with a test solution to which has been added secondary receptors conjugated with a charge label.

6. A method as claimed in claim 1 wherein the receptors or secondary receptors are monoclonal antibodies, polyclonal antibodies, antibody fragments, antibody mimics, chimaeric antibodies viral lysates, recombinant proteins, synthetic peptides, hormones, hormone receptors, single stranded nucleic acids, low molecular weight molecules, chemical compounds conjugated with proteins haptens, fragments of bacterial, plant or animal cells, lectins, glycoproteins or carbohydrates.

7. A method as claimed in claim 1 wherein the electroconductive polymer coating of the sensing electrode has been doped with dopant anions.

8. A method as claimed in claim 7 wherein the dopant anions are dodecyl sulphate or dextran sulphate.

9. A method as claimed in claim 1 wherein steps (b) and (c) are performed simultaneously by contacting the sensing electrode with a test solution to which has been added secondary receptors conjugated with an enzyme label.

10. A method as claimed in claim 1 wherein the sensing electrode comprises adaptor molecules immobilized in or adsorbed to the electroconductive polymer coating thereof and the receptors capable of binding to the analyte to be detected are attached to the said adaptor molecules.

11. A method as claimed in claim 10 wherein steps (b) and (c) are performed simultaneously with a step of contacting the sensing electrode with receptors by contacting the sensing electrode having adaptor molecules immobilised in or adsorbed to the electroconductive polymer layer with a test solution to which has been added receptors and secondary receptors conjugated with a charge label or enzyme.

12. A method as claimed in claim 10 wherein the adaptor molecules are molecules capable of binding to at least one class of receptors capable of binding to the said analyte.

13. A method as claimed in claim 10 wherein the receptors capable of binding to the analyte to be detected are biotinylated, the adaptor molecules are avidin or streptavidin and the receptors are attached thereto via a biotin/avidin or biotin/streptavidin binding interaction.

14. A method as claimed in claim 10 wherein the receptors capable of binding to the analyte to be detected are antibodies, the adaptor molecules are protein A or protein G and said antibodies are attached thereto via a protein A/antibody or protein G/antibody binding interaction.

15. A method as claimed in claim 10 wherein the receptors capable of binding to the analyte to be detected contain a sugar moiety, the adaptor molecules are lectins and the receptors are attached thereto via a lectin/sugar binding interaction.

16. A method as claimed in claim 10 wherein the receptors capable of binding to the analyte to be detected are labelled with FITC, the adaptor molecules are anti-FITC antibodies and the receptors are attached thereto via an FITC/anti-FITC binding interaction.

17. A method as claimed in claim 1 in which biological fluids such as whole blood, serum, lymph, urine, saliva, cerebrospinal fluid or semen are used as the test solution.

18. A method as claimed in claim 1 wherein at least steps (d) and (e) are carried out in a flow-through measuring cell.

19. A method as claimed in claim 10 wherein the step of providing a sensing electrode having adaptor molecules immobilized in the electroconductive polymer coating comprises producing the sensing electrode using a method comprising steps of:
   (a) preparing an electrochemical polymerisation solution comprising monomeric units of the electroconductive polymer and adaptor molecules,
   (b) immersing an electrically conductive electrode in the electrochemical polymerisation solution, and
   (c) applying a cyclic electric potential between the sensing electrode and the electrochemical polymerisation solution to coat the electrode by electrochemical synthesis of the polymer from the solution, said cyclic electric potential being applied for at least one full cycle.

20. A method as claimed in claim 19 wherein the adaptor molecules are selected from the group consisting of avidin, streptavidin, anti-FITC antibodies and a molecule capable of specifically binding to at least one class of receptor molecules.

21. A method as claimed in claim 19 wherein monomeric units of the electroconductive polymer are pyrrole, thiophene, furan or aniline.

22. A method as claimed in claim 19 in which a dopant salt is added to the electrochemical polymerisation solution.

23. A method as claimed in claim 22 wherein the salt is sodium dodecylsulphate or sodium dextran sulphate.

24. A method as claimed in claim 19 wherein the cyclic electric potential has a sawtooth form.

25. A method as claimed in claim 19 wherein the cyclic electric potential is applied for at least two cycles.

26. A method as claimed in claim 19 wherein the cyclic electric potential has a peak value applied to the electrode which is less than or equal to +2 volts.

27. A method as claimed in claim 10 wherein the step of providing a sensing electrode having adaptor molecules adsorbed to the electroconductive polymer coating comprises producing the sensing electrode using a method comprising steps of:
   (a) preparing an electrochemical polymerisation solution comprising monomeric units of the electroconductive polymer,
   (b) immersing an electrically conductive electrode in the electrochemical polymerisation solution,
   (c) applying a cyclic electric potential between the electrode and the electrochemical polymerisation solution to coat the electrode by electrochemical synthesis of the polymer from the solution, said cyclic electric potential being applied for at least one full cycle; and
   (d) contacting the coated electrode with a solution comprising adaptor molecules such that the adaptor molecules are adsorbed onto the electroconductive polymer coating of the electrode.

28. A method of electrochemical detection of an analyte in a sample, which method comprises the steps of:
   (a) providing a sensing electrode having an electroconductive polymer coating, the coating having immobilised therein or adsorbed thereto receptors which are capable of binding to the desired analyte to be detected in the sample;
   (b) contacting the sensing electrode with a test solution comprising the sample so that said analyte binds to said immobilised or adsorbed receptors;
   (c) contacting the sensing electrode with a solution comprising competing molecules capable of binding to said immobilised or adsorbed receptors, said competing molecules being conjugated with a charge label;
   (d) monitoring the electric potential difference between the sensing electrode of part (c) and a reference electrode when both are immersed in an electrolyte; and
   (e) monitoring the electric potential difference between the sensing electrode of part (d) and a reference electrode following a change in the ionic strength of the electrolyte at constant pH.

29. A method as claimed in claim 28 wherein steps (b) and (c) are performed simultaneously by contacting the sensing electrode with a test solution to which has been added competing molecules conjugated with a charge label.

30. A method as claimed in claim 28 wherein steps (b) and (c) are performed simultaneously by contacting the sensing electrode with a test solution to which has been added competing molecules conjugated with a charge label.

31. A method as claimed in claim 28 wherein the sensing electrode comprises adaptor molecules immobilised in or adsorbed to the electroconductive polymer coating thereof and the receptors capable of binding to the analyte to be detected are attached to the said adaptor molecules.

32. A method as claimed in claim 31 wherein steps (b) and (c) are performed simultaneously with a step of contacting the sensing electrode with receptors by contacting the sensing electrode having adaptor molecules immobilised in or adsorbed to the electroconductive polymer layer with a test solution to which has been added receptors and competing molecules conjugated with a charge label or enzyme.

33. A method of electrochemical detection of an analyte in a sample, which method comprises the steps of:

(a) providing a sensing electrode having an electroconductive polymer coating, the coating having immobilized therein or adsorbed thereto receptors which are capable of binding to the desired analyte to be detected in the sample;

(b) contacting the sensing electrode with a test solution comprising the sample so that the said analyte binds to said immobilized or adsorbed receptors;

(c) contacting the sensing electrode with a solution comprising secondary receptors capable of binding to said analyte at a site spatially distinct from the site of binding to immobilized or adsorbed receptors, said secondary receptors being conjugated with an enzyme;

(d) monitoring the electric potential difference between the sensing electrode of part (c) and a reference electrode when both are immersed in an electrolyte; and (e) monitoring the electric potential difference between the sensing electrode of part (d) and a reference electrode following exposure to an electrolyte comprising the substrate for said enzyme.

34. A method as claimed in claim 33 wherein the enzyme is capable of converting a substrate which has no detectable effect on the redox composition of the electroconductive polymer coating of the sensing electrode to a product capable of directly or indirectly affecting the redox composition of the said electroconductive polymer coating.

35. A method as claimed in claim 34 wherein the enzyme is a peroxidase.

36. A method as claimed in claim 34 wherein the product capable of indirectly affecting the redox composition of the electroconductive polymer membrane causes a change in the pH of the electrolyte of part (e).

37. A method as claimed in claim 36 wherein the enzyme is a urease.

38. A method as claimed in claim 33 wherein the enzyme is capable of converting a substrate which has no detectable effect on the redox composition of the electroconductive polymer coating of the sensing electrode to a product which is a substrate for a second enzyme, the action of the second enzyme generating a second product which directly or indirectly affects the redox composition of the electroconductive polymer coating of the sensing electrode.

39. A method as claimed in claim 33 wherein the enzyme is capable of converting a substrate which directly affects the redox composition of the electroconductive polymer coating of the sensing electrode to a product which has no detectable effect on the redox composition of the said electroconductive polymer coating.

40. A method of electrochemical detection of an analyte in a sample, which method comprises the steps of:

(a) providing a sensing electrode having an electroconductive polymer coating, the coating having immobilized therein or adsorbed thereto receptors which are capable of binding to the desired analyte to be detected in the sample;

(b) contacting the sensing electrode with a test solution comprising the sample so that the the desired analyte to be detected in the sample binds to said immobilized or adsorbed receptors;

(c) contacting the sensing electrode with a solution comprising competing molecules capable of binding to said immobilized or adsorbed receptors, said competing molecules being conjugated with an enzyme;

(d) monitoring the electric potential difference between the sensing electrode of part (c) and a reference electrode when both are immersed in an electrolyte; and (e) monitoring the electric potential difference between the sensing electrode of part (d) and a reference electrode following exposure to an electrolyte comprising the substrate for said enzyme.

41. A method of electrochemical detection of an analyte in a sample, which method comprises the steps of:

(a) providing a sensing electrode comprising an electrically conductive electrode coated with a layer of electroconductive polymer with molecules of avidin or streptavidin immobilized therein or adsorbed thereto, said avidin or streptavidin molecules being attached to receptor molecules capable of binding the analyte to be detected attached via a biotin/avidin or biotin/streptavidin binding interaction;

(b) contacting the sensing electrode with a test solution comprising the sample so that said desired analyte binds to said immobilized or adsorbed receptor molecules;

(c) monitoring the potential of the sensing electrode relative to a reference electrode when both are immersed in an electrolyte; and (d) monitoring the potential difference of the sensing electrode relative to the reference electrode following a change in the ionic strength or composition of the electrolyte at constant pH.

42. A method as claimed in claim 41 wherein the analyte to be detected is a nucleic acid and the receptor molecules are oligonucleotides.

* * * * *

UNITED STATES PATENT AND TRADEMARK OFFICE
CERTIFICATE OF CORRECTION

PATENT NO.   : 6,770,190 B1
DATED        : August 3, 2004
INVENTOR(S)  : Milanovski et al.

It is certified that error appears in the above-identified patent and that said Letters Patent is hereby corrected as shown below:

Column 40,
Line 9, delete the second occurrence of "the".

Signed and Sealed this

Eighteenth Day of January, 2005

JON W. DUDAS
*Director of the United States Patent and Trademark Office*